United States Patent
Peterson et al.

(10) Patent No.: US 11,786,158 B2
(45) Date of Patent: Oct. 17, 2023

(54) DEVICES AND METHODS FOR SENSING BLADDER FULLNESS

(71) Applicant: InCube Labs, LLC, San Jose, CA (US)

(72) Inventors: Ralph Walter Peterson, San Jose, CA (US); Kyle Horlen, San Jose, CA (US); Stephen R. Kraus, San Jose, CA (US); Paul Spehr, San Jose, CA (US); Elmar Fischer, San Jose, CA (US); Varghese George, San Jose, CA (US); Mir A. Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 237 days.

(21) Appl. No.: 16/231,331

(22) Filed: Dec. 21, 2018

(65) Prior Publication Data
US 2019/0209067 A1 Jul. 11, 2019

Related U.S. Application Data

(60) Provisional application No. 62/609,090, filed on Dec. 21, 2017.

(51) Int. Cl.
*A61B 5/20* (2006.01)
*A61B 5/00* (2006.01)
*A61B 5/391* (2021.01)

(52) U.S. Cl.
CPC ............ *A61B 5/204* (2013.01); *A61B 5/0059* (2013.01); *A61B 5/0075* (2013.01); *A61B 5/205* (2013.01);
(Continued)

(58) Field of Classification Search
CPC . A61B 5/0059; A61B 5/0075; A61B 5/04882; A61B 5/20; A61B 5/202;
(Continued)

(56) References Cited

U.S. PATENT DOCUMENTS 5,769,791 A * 6/1998 Benaron ............ A61B 17/3417
600/476
5,902,326 A * 5/1999 Lessar .................... A61B 5/076
607/36
(Continued)

FOREIGN PATENT DOCUMENTS

CN 103190885 A 7/2013
CN 103598893 A * 2/2014
(Continued)

OTHER PUBLICATIONS

Yu, et al. "Chronically Implanted Pressure Sensors: Challenges and State of the Field" 2014, Sensors, 14, 20620-20644 (Year: 2014).*
(Continued)

*Primary Examiner* — Patrick Fernandes
*Assistant Examiner* — Anna Roberts
(74) *Attorney, Agent, or Firm* — Brooks Kushman P.C.

(57) ABSTRACT

A bladder fullness monitoring systems includes a controller and an active optical sensor that is affixed to a patient's bladder. The sensor emits light onto the bladder and further detects light reflected from the bladder, in order to generate an output signal that indicates an amount of emitted light was reflected back to the detector. The controller is coupled to the optical sensor to receive and interpret the output signals, e.g., to determine when the bladder is full. The controller may be operatively coupled to a urinary control apparatus which uses the output signals to trigger urination in patients who have lost the ability to voluntarily urinate. Embodiments are particularly useful for monitoring bladder fullness in patients who have lost bladder sensation and/or the ability to voluntary urinate and rely on a urinary control apparatus in order to urinate.

28 Claims, 12 Drawing Sheets

(52) U.S. Cl.
CPC ............ *A61B 5/391* (2021.01); *A61B 5/6837* (2013.01); *A61B 5/6874* (2013.01); *A61B 5/486* (2013.01); *A61B 5/7282* (2013.01); *A61B 5/742* (2013.01)

(58) Field of Classification Search
CPC ......... A61B 5/204; A61B 5/205; A61B 5/207; A61B 5/208; A61B 5/486; A61B 5/6837; A61B 5/6874; A61B 5/7282; A61B 5/74; A61M 2210/1085; A61N 1/36007
See application file for complete search history.

(56) References Cited

U.S. PATENT DOCUMENTS

| | | | | |
|---|---|---|---|---|
| 8,779,361 | B2* | 7/2014 | Costello | H03K 17/941 |
| | | | | 250/338.1 |
| 9,192,763 | B2 | 11/2015 | Gerber et al. | |
| 2006/0008500 | A1* | 1/2006 | Chavan | A61B 5/00 |
| | | | | 607/2 |
| 2006/0276712 | A1 | 12/2006 | Stothers et al. | |
| 2007/0027495 | A1* | 2/2007 | Gerber | A61N 1/36007 |
| | | | | 607/41 |
| 2007/0123778 | A1* | 5/2007 | Kantorovich | A61B 8/465 |
| | | | | 600/437 |
| 2009/0163819 | A1* | 6/2009 | De Kok | A61B 5/444 |
| | | | | 600/476 |
| 2013/0018281 | A1* | 1/2013 | Nagale | A61B 5/208 |
| | | | | 600/587 |
| 2017/0035342 | A1* | 2/2017 | Elia | A61B 5/14507 |
| 2018/0008185 | A1 | 1/2018 | Ramu | |
| 2018/0009195 | A1 | 1/2018 | Ramu et al. | |
| 2018/0263558 | A1* | 9/2018 | Cronin | G16H 40/63 |

FOREIGN PATENT DOCUMENTS

| | | |
|---|---|---|
| CN | 103598893 B | 2/2014 |
| CN | 103610467 A | 3/2014 |
| CN | 103598893 | 2/2016 |
| CN | 103598893 B | 2/2016 |
| CN | 102441232 A | 5/2023 |
| JP | H071903 U | 1/1995 |

OTHER PUBLICATIONS

U.S. Appl. No. 15/410,692, filed Jul. 20, 2017, Imran, Mir.
ISR and Written Opinion in PCT/US2018/067387 dated May 14, 2019.
Extended European Search Report in EP App. No. 18892362 dated Oct. 21, 2021.
Notice of Reason for Rejection re Japanese Patent App. No. 2020-533235 dated Oct. 18, 2022.

* cited by examiner

DEVICES AND METHODS FOR SENSING BLADDER FULLNESS

CROSS-REFERENCE TO RELATED APPLICATIONS

This application claims the benefit of priority of U.S. Provisional Patent Application Ser. No. 62/609,090, entitled "Devices And Methods For Sensing Bladder Pressure, filed Dec. 21, 2017, which is fully incorporated herein by references for all purposes.

FIELD OF INVENTION

Embodiments of the invention relate to medical apparatuses and methods, and more specifically, to a system and method for sensing bladder fullness.

BACKGROUND

Many disorders can result in loss of a patient's ability to voluntarily control bladder function. Most commonly, patients suffering from spinal cord injuries can lose not only the ability to voluntarily control urination, but also the ability to sense when the bladder is full. Such patients have usually had to rely on the chronic use of urethral catheters, such as Foley catheters, which are extended through the patient's urethra until an end segment of the catheter reaches the bladder, where it can draw in urine and void the bladder. However, urethral catheters have a number of drawbacks. In particular, the use of urethral catheters presents a constant risk of infection for the patient, as such catheters can introduce contaminants, cause trauma or fail to adequately void the bladder. Moreover, urethral catheters usually drain into a bag which the patient must carry when away from home or a treatment facility. Patients often resist using urethral catheters, raising risks of infrequent voiding and infection.

For patients who suffer from spinal cord injuries, the problems raised with the use of urethral catheters are exacerbated. Foley catheters, for example, require frequent exchange by the patient. The exchange of urethral catheters is a sensitive manual task which is at best difficult, if not impossible for patients who suffer from spinal cord injuries.

Various attempts have been made to address some of the deficiencies of urethral catheters. For example, pudendal nerve stimulation systems allow patients and their caregivers to selectively stimulate the pudendal nerves to control voiding of the bladder. However, such pudendal nerve stimulation systems do not detect fullness of the bladder, and therefore cannot alert the patient that their bladder is full. For those patients who have lost the ability to sense when their bladder is full, conventional pudendal nerve stimulation systems raise the risk that the patient may wait too long to void his or her bladder, raising risk of infection to the patients. The inability of conventional pudendal nerve stimulation systems to detect fullness is particularly problematic, because the frequency between when a patient's bladder becomes full can vary significantly, for numerous reasons which the patient may not be aware of, such as the patient's recent fluid intake, hydration level, and/or diet.

SUMMARY OF THE INVENTION

Various embodiments of the invention provide for a bladder monitoring system for providing real-time information on the degree and/or state of fullness of a patient's bladder. The system can include a sensor device and a controller. The sensor device can be affixed to an external wall of the bladder without piercing an internal wall of the bladder. By not being placed in the bladder or piercing the internal wall of the bladder, the sensor device can reduce the risk of infection associated with conventional methods for measurement of bladder pressure or fullness.

In many embodiments, the sensor device can include a light emitter and a detector. The light emitter can be positioned to emit light at the external wall of the bladder, and the detector can be positioned to detect the emitted light reflected off the external bladder wall. Further, the sensor device can generate an output signal that is indicative of an amount of the reflected emitted light. The controller can be operatively coupled to the sensor and can include logic to determine a degree of bladder fullness based on the output signal of the sensor device. In this way, the bladder monitoring system can be particularly useful for those patients who have lost the ability to sense bladder fullness and/or to voluntarily urinate due to spinal cord injury or other condition affecting the functionality of one or more of their spinal cord, pudendal nerves or other neural pathway involved in the urination process.

In some examples, the controller can be configured to notify the patient (e.g., mobile phone notification) when the determined degree of bladder fullness exceeds a threshold. In addition, the controller can be configured to cause an associated urinary control apparatus to induce micturition. In variations, the controller can be integrated with or separate from the urinary control apparatus.

In other examples, the sensor device can determine a concentration of chromophores in the bladder fluid of the patient. In such examples, the sensor device can emit light onto the patient's bladder wall at multiple wavelength ranges and can detect the light scattered by the fluid of the bladder for each respective wavelength range. The concentration of chromophores for each respective wavelength range can be determined and monitored by a controller for changes in relation to one another to detect, for example, changes in color in urine collected by the bladder.

A key advantage provided with some examples over other sensor technologies is that such examples can determine bladder volume using an optical sensor that does not need to be positioned in the bladder by catheterization, that is, it does not need to be attached to a Foley catheter or like device that is permanently left in place in the patient's urinary tract (this is advantageous since it reduces the risk of infection associated with Foley catheters). Instead, in various embodiments, an active optical sensor can be attached directly to the bladder wall (e.g., using a suture or other attachment means known in the medical arts). Also, according to some embodiments, the optical sensor can be implanted with an associated electrical stimulation apparatus or system configured to provide for electrically evoked urination and then function without any further action required by the patient.

Examples can further attach the optical sensor to the bladder in various alternative configurations. In particular examples, the optical sensor can be sutured to the outer surface of the bladder wall, so as to not pierce or otherwise penetrate the bladder wall. Such embodiments avoid the risk of infection or mineralization (e.g. deposition of minerals resulting in the formation of stones in the bladder) which would occur from an electrode or other sensor which is required to pierce the bladder wall. The optical sensor can also be configured to be sutured to a single or multiple points on the surface of the bladder during implantation so as to minimize trauma or injury to the bladder.

Embodiments are also particularly useful for monitoring and providing information on the degree of fullness of a patient's bladder for those patients who have lost the ability to sense bladder fullness and/or voluntarily urinate due to spinal cord injury or other condition affecting the functionality of one or more of their spinal cord, pudendal nerves or other neural pathway involved in the urination process. As the optical sensor does not require high voltage or magnetic fields to function (being based on the emission and collection of scattered light), it can be powered by a low voltage long lasting battery which may be configured to be rechargeable by induction coupling with a charging device placed on or near the surface of the abdomen.

For a fuller understanding of the nature and advantages of the present invention, reference should be made to the following detailed description taken in conjunction with the accompanying drawings. The drawings represent embodiments of the present invention by way of illustration. Accordingly, the drawings and descriptions of these embodiments are illustrative in nature and not restrictive.

DETAILED DESCRIPTION

Embodiments as described include devices, systems and methods for detecting bladder fullness in a patient and providing information on such. Some embodiments include an optical based sensor system for measuring and providing real-time information relating to the patient's bladder fullness based on, for example, bladder distention due to urine volume.

As used herein the term, "about" means within ±10% of a stated property, dimension or other value and, more preferably, ±5% of the stated value. Also, as used herein, the term "substantially" means within ±10% of a stated property or quality, more preferably, ±5% of the stated value.

Some embodiments include sensors for continuously monitoring a patient's bladder for degree and/or signs of fullness in order to initiate urination (aka micturition) for patients who have lost voluntary bladder control and/or the ability to sense bladder fullness, such as patients who have sustained a spinal cord injury. In some embodiments, a bladder monitoring system is coupled to or otherwise integrated with a urinary control apparatus, such that the bladder monitoring system generates a micturition trigger for the urinary control apparatus.

Embodiments as described provide for a bladder monitoring system that can respond to fullness of the bladder, rather than at timed intervals, as provided by some conventional approaches. Among other benefits, embodiments as described better accommodate factors that can affect the fullness of the patient's bladder (e.g., hydration), thus avoiding risk of over-extending the time period between the patient's voiding, while providing more convenience and efficiency.

Embodiments as described provide for a bladder monitoring system to monitor a patient's bladder for fullness, and to provide the patient with feedback to indicate when the patient's bladder should be voided. A bladder monitoring device as described by examples can benefit urinary functions of patients with various types of disorders. For example, for patients who use urethral catheters to empty their bladder (e.g., Foley catheter) but who also lack ability to detect bladder fullness (e.g., patients with spinal cord injuries), an example bladder monitoring system can detect when voiding of their bladder should occur, and in at least some aspects, optimize the frequency between when the patient voids his or her bladder so as to reduce the probability of infection. For patients who use pudendal nerve stimulation systems, a bladder monitoring system as described can provide notification to the patient and caregivers. Still further, an example bladder monitoring device can be used to trigger a pudendal nerve stimulation system to induce voiding of the patient's bladder.

Figure 1A:
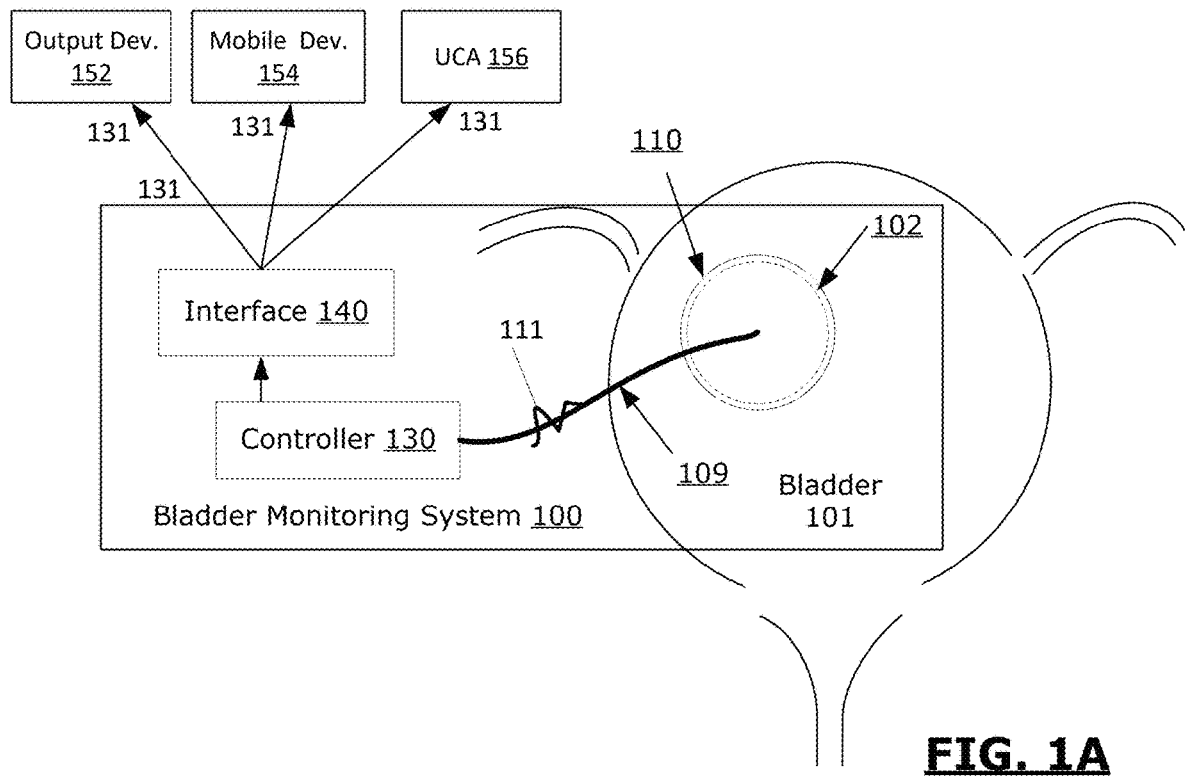
FIG. 1A illustrates an example of a bladder monitoring system, according to one or more examples.
Figure 1B:
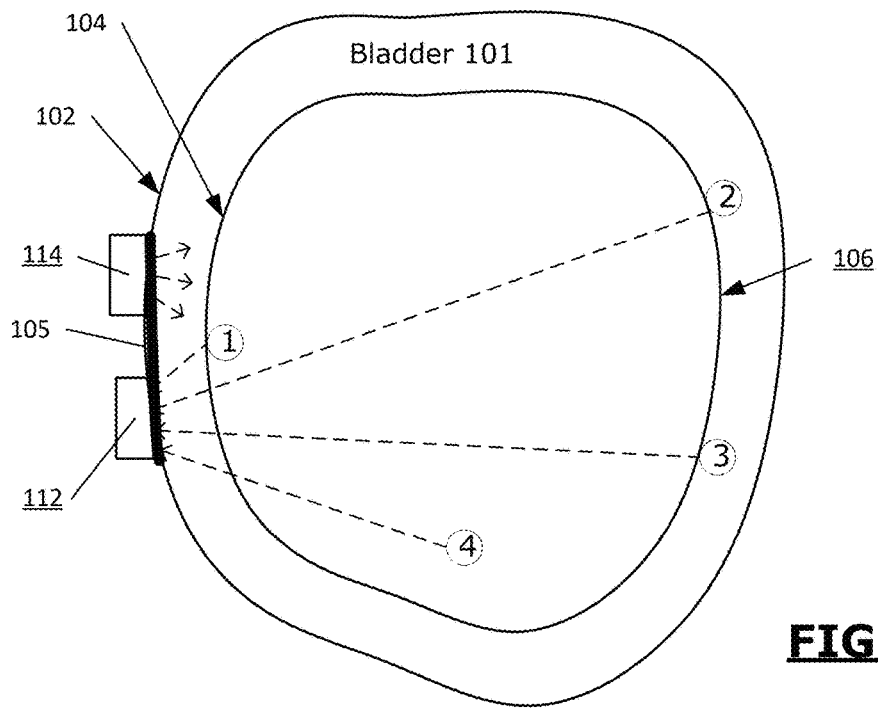
FIG. 1B illustrates example modes of light scattering for an example bladder monitoring system of FIG. 1A.

FIG. 1A and FIG. 1B illustrate an example bladder monitoring system, according to one or more examples. An example bladder monitoring system 100 includes an optical bladder volume sensing device ("BVSD") 110, a controller 130 and a communication interface 140. The BVSD 110 can be positioned within the patient's body so as to be affixed to or in near proximity of the patient's bladder 101. When positioned, the BVSD 110 generates an output signal 111 that is interpretable by the controller 130 as a measurement of bladder volume. To generate the output signal 111, the BVSD 110 includes an active optical sensor that emits light and detects reflection. In some embodiments, the output signal 111 can be in the form of a voltage signal, where the value of the voltage signal is indicative of a bladder volume level or measurement. As an addition or variation, the output signal 111 can reflect a pattern or other characteristic that is interpretable as a measurement of bladder volume.

The controller 130 can be communicatively coupled to the BVSD 110 to receive the output signal 111. In some implementations, the controller 130 is implanted within the patient's body, in operable proximity to the BVSD 110 (e.g., under the patient's skin). In such embodiments, the controller 130 can be directly connected to the BVSD 110 to receive the output signal 111 (e.g., via a communication cable 109). In other variations, the controller 130 can be wirelessly coupled to the BVSD 110 to receive the output signal 111. The controller 130 can interpret the output signal 111 and generate a corresponding output that can be acted on, such as to trigger or otherwise cause voiding of the bladder 101 by the patient, caregiver, or an associated urinary control apparatus, as indicated by the controller's output 131. In examples, the output 131 can be communicated to the communication interface 140, which in turn transmits or otherwise communicates the output to, for example, an associated output device 152 (e.g., notification device with light or speaker), mobile device 154 (e.g., notification for patient or caregiver), or an associated urinary control apparatus 156. In the latter case, the output 131 can act as a trigger for the associated urinary control apparatus 156. Moreover, while specific embodiments are described in which the controller 130 is positioned in situ, in variations, the controller 130 can be positioned outside of the patient's body. An example of a urinary control apparatus 156 is described with U.S. patent application Ser. No. 15/410,692, entitled Systems And Methods For Patient-Enabled Bladder Control, with the aforementioned application being hereby incorporated by reference in its entirety for all purposes.

In other variations, the controller 130 may be indirectly coupled to the BVSD 110 to receive the output signal 111. For example, the BVSD 110 can communicate the output signal 111 directly to the communication interface 140, which in turn communicates the output 111 to the controller 130. In such embodiments, an electrical connection (e.g., cable) may extend between the BVSD 110 and the communication interface 140, and a separate connection (e.g., cable, wireless connection) can extend between the communication interface 140 and the controller 130. In such embodiments, the controller 130 may be positioned outside of the patient's body, while the communication interface 140 is positioned inside the patient's body (e.g., under the skin).

Still further, while some embodiments describe the controller 130 as being a separate device, in variations, some or all of the functionality of the controller 130 can be integrated with the BVSD 110. For example, in some implementations, the BVSD 110 can include micro-circuitry and/or integrated logic to interpret a raw sensor output of the BVSD 110. As an addition or variation, the BVSD 110 can also include a transceiver to wirelessly communicate with the controller 130, to the communication interface 140, or alternatively, with the controller 130 positioned outside of the patient's body.

Upon receiving the output signal 111 (or a corresponding signal thereof from an intermediary device), the controller 130 can generate an output 131 that is indicative of a determination of bladder volume. In some embodiments, the output of the controller 130 is binary, so as to indicate one of "full" or "not full". In other variations, the output 131 of the controller 130 can indicate levels of fullness for the patient's bladder 101 (e.g., "empty", "partially full", "full" and "very full"). Still further, in other embodiments, the output of the controller 130 can be in the form of a score, such as from 1 to 10, indicating the level of bladder fullness.

According to some embodiments, the BVSD 110 is structured to attach or otherwise affix to the external wall 102 of a bladder 101. When affixed, the position of the BVSD 110 relative to the bladder 101 may be constant (e.g., the BVSD 110 can move with the bladder volume, but remain in same substantially same position with respect to the bladder 101).

In variations, the BVSD 110 can be positioned a set distance from the external bladder wall 102. Still further, in other variations, the BVSD 110 can be positioned inside the bladder 101, on or near an internal bladder wall 104.

In embodiments in which the BVSD 110 is affixed to the external wall 102 of the bladder 101, the BVSD 110 may include at least suture openings. The suture openings can receive sutures that serve to fix the BVSD 110 to the external wall 102 of the bladder 101. In some embodiments, the suture openings are dimensioned to receive sutures that are sufficiently dimensioned (e.g., cross-diameter) to prevent penetration or piercing of the external bladder wall 102. In variations, the suture openings may alternatively receive sutures to affix the BVSD 110 to the internal wall 104 of the bladder 101. Still further, in some embodiments, the BVSD 110 can include a base structure, thickness or surface 105 that is shaped to be affixed to the internal bladder wall 104. The base surface 105 can, for example, be smooth and/or coated to avoid irritation. Additionally, the base surface 105 can be structured to promote or otherwise enable sensing from within the BVSD 110. For example, portions of the base surface 105 can be translucent to promote light transmission from the emitter 114, and light detection for the detector 112. By attaching the BVSD 110 to the external wall 102, the BVD 110 can have a relatively unobstructed sensing view of the bladder 101, free from tissue, fluid, or dynamic particulates that can cause inaccuracies with respect to the measurements.

In embodiments such as depicted by FIG. 1A, the controller 130 is implanted to connect to the BVSD 110 via a wire or bundle of wires of cable 109 (e.g., insulated cable). The controller 130 may include a microprocessor, integrated circuitry or other logic to interpret the output signal 111 of the BVSD 110. In some variations, the controller 130 can also include a separate or integrated power controller to control light transmission by the BVSD 110.

In some embodiments, the controller 130 receives an electrical output from the BVSD 110 while the patient's bladder 101 is in both an empty state and a full state. The changes to the volume of the bladder 101 for the respective empty and full states, as well as intermediate states, can be reflected by a change in an electrical characteristic of the output signal 111. In some embodiments, the change in bladder states can be reflected by a change in voltage level for the output signal 111. The change in the voltage value can further be correlative to the change in the volume of the bladder 101. When, for example, a percentage change in the electrical output from the BVSD 110 exceeds a predetermined threshold, the controller 130 can determine the bladder 101 to be full. In other implementations, additional thresholds can be used to mark additional thresholds. In some embodiments, the electrical output from the BVSD 110 for the patient's bladder 101 in the empty and full state can also be used to calibrate the readings that are made of the BVSD 110.

According to some embodiments, the electrical output is derived from a photocurrent generated by a photodiode of the BVSD 110 (e.g., light detector 112). The photodiode can respond to detected light by producing a photocurrent, which in turn, can be developed into a sensed voltage potential that is then correlated to the fullness of the bladder 101. The predetermined threshold can be based on the percentage change in the electrical output of the BVSD 110 between bladder volume s representing "empty" and a degree of fullness (e.g., half full, full, etc.).

In some embodiments, the controller 130 is able to interpret the output signal 111 of the BVSD 110 as a measurement of the sum of one or more optical scattering values for various constituents of the bladder 101 (e.g., cells comprising the bladder 101 lumen, mucosa, submucosa, muscularis, serosa, adventitia, and interstitial regions between cells, etc.). Measurements of the optical scattering values of the bladder 101 may vary due to the level of fullness of the bladder 101. For example, one or more of the optical scattering values can correlate to a level of fullness of the bladder 101, and more specifically, to a thickness of the bladder wall. Specifically, as the bladder becomes fuller, the bladder walls stretch, thereby causes the cell layers, as well as the interstitial regions between cells, to become thinner. As the bladder walls stretches, the changes to the bladder wall can affect the amount of light that is scattered versus reflected, with greater scattering meaning less reflected light, and a decrease of the output signal 111. However, embodiments of the invention further recognize that the amount of reflected light that is measured as between the full and empty bladder states can include contributions that are attributable to different physiological changes, and further that the contributions can be both conflicting contributions and combining contributions. For example, while the expanding bladder 101 may cause more emitted light to scatter, the nature of the volume expansion, the region where emitted light is reflected and/or other physiological changes can cause scattering that results in the emitted light being indirectly reflected back to the detector 112 (e.g., light bounding off of multiple locations in the exterior bladder wall 102). In this way, the difference in output measurements between a full bladder and an empty bladder establishes a range or delta (herein "Δ") from which measurements taken during real-time monitoring of the fullness of the bladder can be gauged. In some implementations, the value range for the amount of light detected can be deemed a proportional indicator of bladder volume. For example, greater bladder volume can result in lesser light being detected (and thus lesser photovoltaic voltage generation from the detector 112). In other variations, the value range for the amount of light detected can be patterned matched, to account for conditions such as the increase in bladder volume causing the emitted light to reach a local minimal inflection point, followed by a period of increased value for light detection, as a result of the amount of light scatter that indirectly reflects back to the detector 112. Such a condition may occur as a result of physiological conditions that create a condition in which the amount of light scatter that indirectly reflects back to the detector 112 is equal to or greater than the amount of light scatter that results in light being deflected away from the detector 112. As illustrated by such embodiments, the sensed optical characteristics, as generated from reflected light, can vary in correlation to the volume and thus fullness of the bladder. Moreover, the sensed optical characteristics can correlate to other conditions, such as conditions in which the elasticity of the bladder wall (e.g., decrease in elasticity) is changed.

In many embodiments, the system 100 can operate under the assumption that the sensed optical characteristics, as generated from reflected light, can vary in a manner that is correlative to the relative thickness of the bladder wall, which in turn, is indicative of a volume of the bladder 101. In some instances, an approximately 30% change in the electrical output (e.g., magnitude of the output signal 111 from the BVSD 110) received by the controller 130 may translate to an approximately 400 mL change in bladder liquid volume. As mentioned, other changes in the electrical output and its corresponding volume change have been observed, and embodiments recognize that alternative correlative techniques can be employed to match changes in the electrical output to bladder fullness and/or other physiological changes.

Upon determining that the percentage change in an electrical output received from the controller 130 exceeds the predetermined threshold, the controller 130 may generate the output signal 131, such as to signal the communication interface 140 to notify the patient or caregiver of the fullness level of the bladder (e.g., via the notification device 152 or mobile device 154). In addition, the controller 130 may continue to monitor the bladder 101 to detect when the output signal 131 is indicative of a voided bladder (e.g., output signal 131 reaches a minimum threshold value). In response to detecting that the bladder is voided, the controller 130 can also provide a notification to the notification device 152 and/or the mobile device 154 to notify the patient or caregiver as to when the bladder is voided to an acceptable residual volume (e.g., empty, near empty, etc.) so that manual voiding can cease.

As an addition or alternative, the controller 130 may generate the output signal 131 to trigger the urinary control apparatus 156 to stimulate voiding (e.g., using an alternative implant that signals the penal nerve for the patient). Additionally, the controller 130 can continue to monitor the bladder 101 to detect when the output signal 131 is indicative of a voided bladder 101. Once, for example, the output signal 131 reaches the threshold value associated with the voided bladder 101, the system 100 can trigger the urinary control apparatus 156 to cease stimulation of the bladder 101. In this way, based on feedback from the BVSD 110 for initiating and ceasing voiding of the bladder 101, the system 100 creates a closed loop system for regulating fullness levels of the bladder 101. Moreover, in some embodiments, upon determining that the percentage change in the output received by the controller 130 exceeds the predetermined threshold, the controller 130 may cause an associated implant 140 to induce micturition.

In variations, the system 100 may be utilized as a diagnostic tool to determine the presence of abnormal levels of bacteria, blood or protein in the urine of a patient (e.g., such as might occur from urinary infection, kidney disease, etc.). According to some embodiments, the system 100 may be configured to characterize a relative concentration of bacteria, protein, blood or other chromophores present in the urine within the bladder 101 and/or the bladder 101. For example, system 100 may be configured to perform a spectroscopic analysis for detecting one or both by tuning the BVSD 110 to operate, for example, in the ultraviolet range (e.g., <400 nm wavelength) where bacteria and protein have the highest optical absorption. In other embodiments, for example, the system 100 may be configured to tune the BVSD 110 to a wavelength range that includes well-established absorption peaks for oxyhemoglobin and deoxyhemoglobin (e.g., between 532 nm and 585 nm) to detect a presence of blood in the fluid of the bladder 101. In this way, the BVSD 110 can detect any color change in the fluid contained within the bladder 101 or in the relative chromophore content in the tissue of the bladder wall.

FIG. 1B illustrates embodiments of the BSVD 100 in operation on a patient's bladder 101 as part of the bladder monitoring system 100, according to one or more embodiments. The BVSD 110 includes a light source or emitter 114 and a light detector 112, where the emitter 114 emits light onto the exterior bladder wall 102, and the detector 112 is positioned to detect emitted light that is reflected from the bladder 101. In some embodiments, the BVSD 110 can be operated so that the light emitted from the emitter 114 can penetrate to reach varying depths and/or internal features (e.g., interior walls) of the bladder 101, before a significant portion of the light is scattered or reflected back to the detector 112. In some embodiments, the amount of emitted light that is reflected from the interior of the bladder 101 and then detected by the detector 112 can form the basis of the output signal 111 generated by the BVSD 110. Embodiments of the invention recognize that in some cases, the reflected light can include contributions from light that scatters but indirectly reflects back to the detector 112, such as emitted light that is initially scattered within the bladder 101, but then undergoes a series of deflections to return to the detector 112. Conversely, the difference in the amount of emitted light versus detected light can include light that passed through the bladder 101 and/or light that scatters or otherwise deflects away from the detector 112. Still further, in some embodiments, the controller 130 can operate under a configuration in which a fullness of the bladder 101 is directly and inversely proportional to the amount of emitted light that is reflected back to the detector 112. Accordingly, the output signal 111 of the BVSD 110, which may be based on the amount of light that is detected by the detector 112, may also be inversely proportional to the fullness of the bladder 101.

In various embodiments, the BVSD 110 is operable so that the emitter 114 emits light to targeted regions within the bladder 101. The operation of the BVSD 110 may be modal, so that the depth and direction of the emitted light results in at least some of the emitted light reflecting at the target region. As illustrated with embodiments, by selecting a target region for directing emitted light (e.g., using direction, intensity and/or wavelength properties of the emitted light), different types of information can be determined about the patient's bladder 101, including information relating to the fullness of the bladder 101.

In a first mode, the emitter 114 targets emitted light to a region 1 that is between an external wall 102 and an internal wall 104 of the bladder. When the emitter 114 emits light to this target region, a direct and inverse correlation exists as between the amount of light that is reflected back to the detector 112 and the fullness of the bladder 101 (e.g., caused by the bladder 101 stretching and/or becoming thinner from an increase in its volume).

In a second mode, the emitter 114 targets emitted light to a region 2 that coincides with a distal interior wall of the bladder 101. In this mode, the light emitted by the BVSD 110 may, at least initially, not pass through any fluid that is retained in the bladder 101. As such, the controller 130 may determine a time of flight measurement based on the light reflected back from the distal wall. For example, the time of flight measurement may be used to calculate the distance between a proximal wall (e.g., a portion of external bladder wall 102) and a distal wall (e.g., 106) of the bladder 101 relative to the BVSD 110. As an addition or variation, the time of flight measurement may provide a baseline that that can be used as a basis for comparison when the bladder 101 expands with fluids. Accordingly, in some embodiments, the calculated distance may be input as part of a calculation to determine the bladder volume. By way of example, during initial filling (e.g., first quarter of the fill), utilizing light that targets the distal wall of the bladder 101 can account for a sharp decrease in the output signal 111 of the BVSD 110, because value of the signal from light detector 112 can reflect, for example, a light intensity reduction that is the result of an increase in distance traveled by the light (e.g., distance between a proximal portion of external bladder wall 102 and distal wall 106 increases as the bladder 101 fills, causing reflected light to travel farther, with greater loss of intensity). As the bladder 101 continues to fill and the fluid level of the bladder 101 rises above the light detector location, the reflected light may scatter away from the detector 112, so as to go undetected, further diminishing the electrical output of the BVSD 110. Moreover, the presence of the fluid medium may reduce the amount of light scattering that indirectly reflects back to the detector 112.

In a third or alternative mode, the emitted light can be directed to a region 3 in the bladder that contains fluid. The detector 112 can be indicative of light scattering (e.g., by loss of light reflected back to the detector), and the detection can correlate to an optical mismatch as between either a proximal portion of external bladder wall (e.g., 102), a distal wall 106 and the liquid content of the bladder 101. Light sensed in this mode may be proportional to the differences in refractive index between the bladder wall tissue and the liquid contents of the bladder 101. The controller 130 can correlate information indicating difference in refractive index to conditions of the patient's bladder 101, including of fullness of the bladder 101.

In a fourth mode, light is directed to a region 4, where it may be scattered by solids present in the liquid bladder volume. Light detected by the BVSD 110 in this mode may represent the concentration of protein, bacteria, hemoglobin, and any other chromophore that is present in the liquid bladder volume. While this mode is not directly applicable to determining bladder volume, this mode may provide additional diagnostic features discussed in more detail below (e.g., urinary infection, kidney disease, etc.).

In some variations, a dye contrast agent may be introduced into a wall of the bladder 101 at the implantation site (e.g., area under the BVSD 110). By introducing a dye contrast agent, the optical scattering coefficients of the cells and the interstitial regions of the cells in the bladder 101 may increase and cause an associated increase in the change measured for "empty" and "full" representations of the bladder 101. Dye contrast agents may be introduced by tattooing the implantation area with, for example, India ink (e.g., Spot®, Endomark®, etc.), indocyanine green (e.g., Cardiogreen®), etc.

Figure 2:
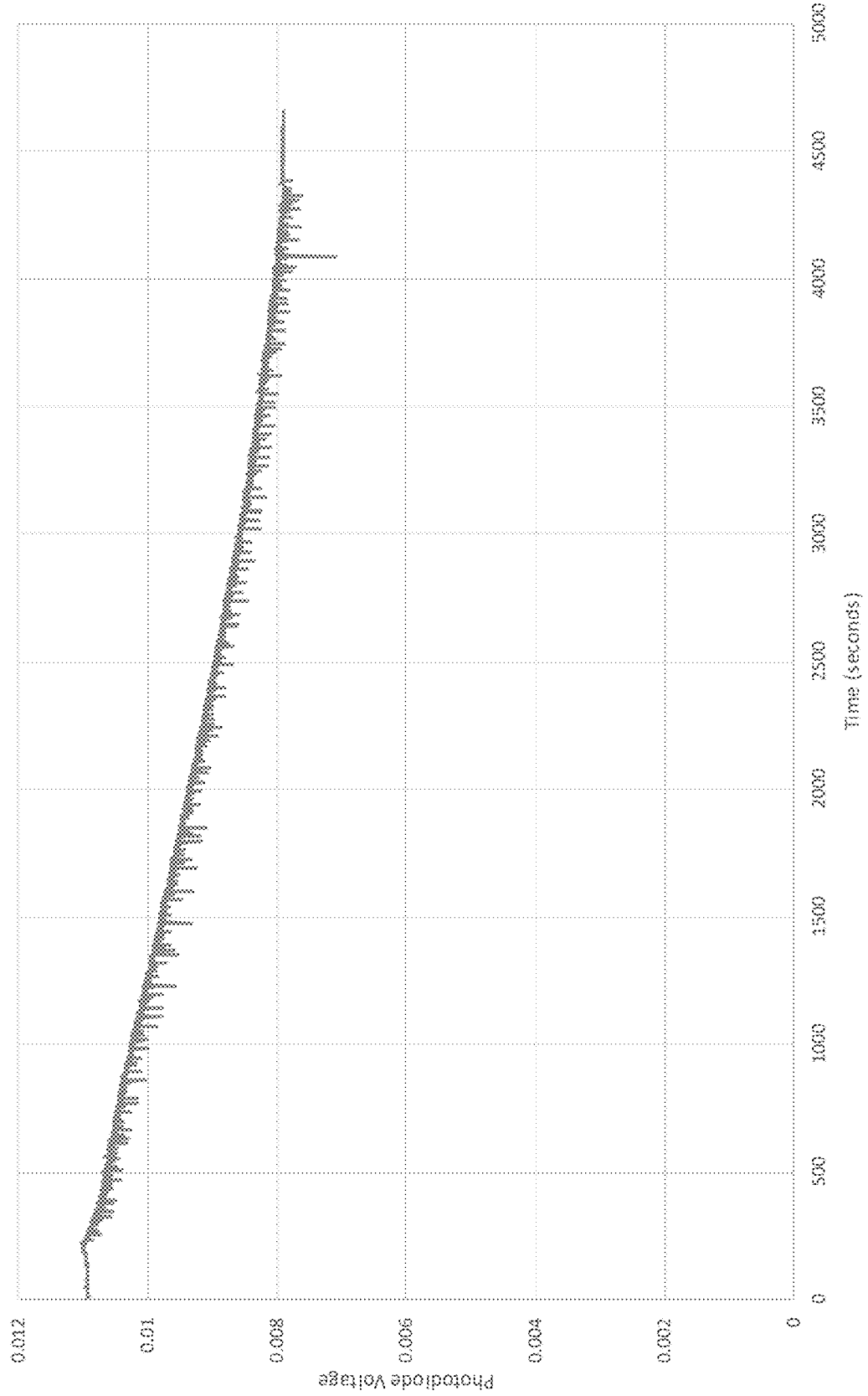
FIG. 2 is a graph of changes in an electrical signal versus bladder fill time, in accordance with an example bladder monitoring system of FIG. 1A.

FIG. 2 is a graphical representation of the electrical signal of the BVSD 110 over time as the bladder becomes fuller. With reference to FIGS. 1A, 1B and 2, the BVSD 110 generates the electrical output 111 as a voltage output, with the voltage value reflecting an amount of emitted light that reflects back from a target region (e.g., external wall) of the bladder. In some embodiments, the controller 130 implements logic that correlates the condition of the bladder becoming full with the amount of reflected light that is reflected back to the detector 112, with the relationship being one that is inversed. As an addition or variation, the controller 130 implements logic that correlates light scattering with the fullness of the bladder, where, for example, the amount of light scattering is indicated by a strength of the signal emission from the BVSD 110, such that the signal strength is inversely related to the amount of scatter. In embodiments, the output signal 111 of the BVSD 110 can be in the form of a voltage output, such that the voltage level of the output signal 111 is inversely related to the fullness of the bladder. As shown in the graph of FIG. 2, as the bladder volume changes between empty and full bladder states over time, the output signal 111 of the BVSD 110 decreases. For example, in FIG. 2, the output signal 111 of the BVSD 110 decreases from about 0.011V to about 0.008V, representing an increase in volume of the bladder by about 33%.

Figure 3A:
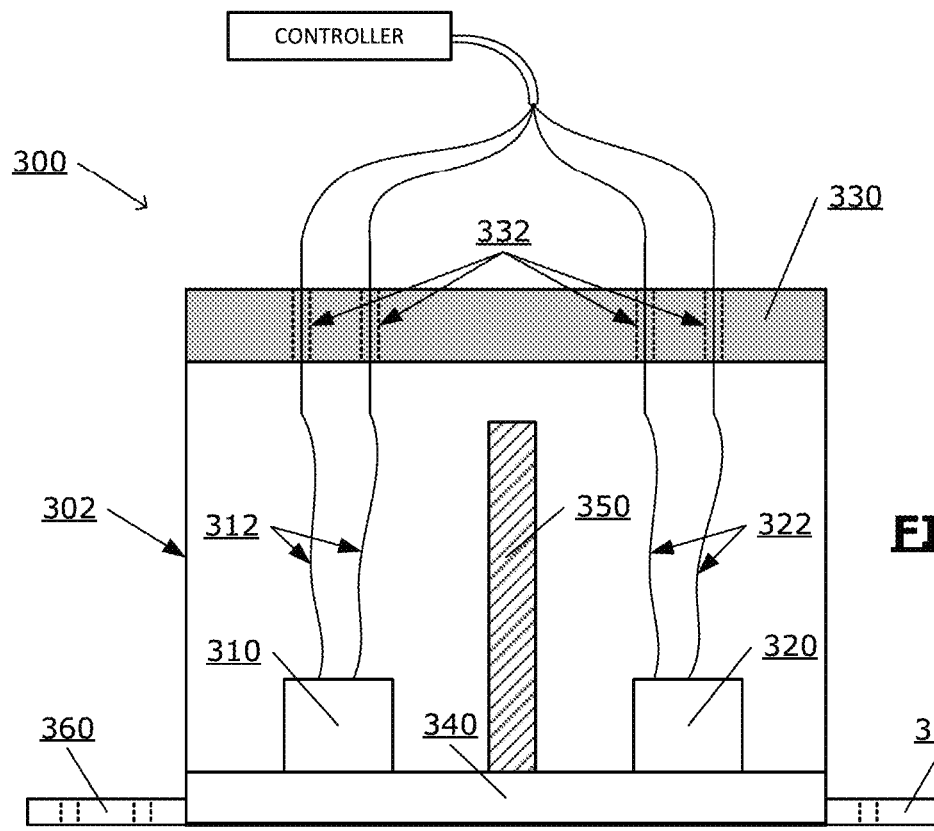
FIG. 3A illustrates an example of a sensor to monitor fullness of a bladder of a patient.

FIG. 3A illustrates an embodiments of a BVSD for use in monitoring bladder fullness. The BVSD 300 includes a light source 310 (also referred to herein as an emitter 310), a light detector 320, a backing 330, an optical window 340, a light barrier 350 and a suture skirt 360. A side wall 302 of BVSD 300 can be formed out of any biocompatible material (e.g., titanium) conducive to providing a hermetic seal for the light source 310 and the light detector 320.

The light source 310 may correspond to any light source that emits light when activated (e.g., light-emitting diode). As an addition or variation, the light source 310 may be tuned to any wavelength (e.g., ultraviolet, visible, near infrared, infrared, etc.). In some implementations, the BVSD 300 utilizes infrared light wavelength emissions to determine a change between an empty and a full bladder. In addition, the light source 310 may include one or both of incoherent and coherent light sources (e.g., LED, laser, etc.). For example, in some variations, a coherent light source may be utilized to provide greater tissue penetration, such as of a distal wall of the bladder (e.g., 106 of FIG. 1B).

The light detector 320 may correspond to any device to detect light and convert the light into an electrical output (e.g., photodiode voltage). For example, light emitted by the light source 310 may be scattered by the bladder tissue and detected by the light detector 320, and the light detector 320 may then generate a photocurrent that is proportional to an increase in volume of the bladder.

As depicted in FIG. 3A, or FIG. 4A through FIG. 4H, in some variations, the light source 310 and/or the light detector 320 may be mounted and positioned on the optical window 340/440, or on a non-tissue contacting surface (e.g., positioned opposite to the optical window 340/440) of the BVSD 300 (e.g., such as shown by backing 330). In variations, the light source 310 may be mounted on the backing 330, while the light detector 320 may be mounted on the optical window 340, or vice versa.

The backing 330 may be formed from any material suitable for mounting the light source and detector 310, 320 as a pair. The backing may also be formed of material that can form a hermetic seal for the various components of the BVSD 300 (e.g., ceramic material, etc.), when the BVSD 300 is affixed to the bladder. The backing 330 may also include feedthroughs 332 for guiding the conductive wire 312/322 from an internal or encapsulated space within the BVSD 300 to a region outside the BVSD 300 in order to facilitate a direct or indirect connection to a controller or other device.

Referring now to FIG. 3A, optical window 340 may be formed from any optical material (e.g., sapphire) that provides a transparent medium to transmit light to/from the BVSD 300. The optical window 340 may be configured to allow for transmission of a range of wavelengths (e.g., ultraviolet, visible, near infrared, etc.) utilized by the BVSD 300. For example, in one variation, the BVSD 300 may utilize light in the ultraviolet range (e.g., <400 nm), where bacteria and protein have the highest optical absorption in order to perform a spectroscopic analysis of the fluid content of the bladder (e.g., determine the relative concentrations of chromophores present in a bladder).

According to many embodiments, the optical window 340 may be configured as a rigid structure including, for example, a flat structure. In variations, the optical window 340 may be a curved or flexible structure configured to provide for the arrangement and/or quality of the optical window 340 that is substantially flush (or fully pressed) against an external wall of the bladder. The arrangement of the optical window 340 being flush with the external wall of the bladder prevents or at least minimizes the introduction of fluid between the tissue contacting surface of the BVSD 300 and an external wall of the bladder. The introduction of fluid between the tissue contacting surface of the BVSD 300 and the bladder wall may yield inaccurate measurements since the optical properties of the fluid may not be altered with changes in the distention of the bladder, which may lead to changes in the elasticity of the bladder wall going undetected.

The light barrier 350 may include any material provided to minimize or prevent a direct transmission of light between the light source 310 and the light detector 320 (e.g., opaque material, photochromic material, etc.). In the embodiment of FIG. 3A, the light barrier 350 contacts the optical window 340 but does not contact the backing 330. In some configurations, the light barrier 350 can be structured to contact both the optical window 340 and the back 330. In other configurations of the BVSD 300, the light barrier 350 may extend into the optical window 340 to the tissue-contacting surface of the BVSD 300 (as depicted in FIG. 4C and FIG. 4H) or may contact the optical window 340 without extending into the optical window 340 (as depicted in FIG. 3A, FIG. 4D and FIG. 4G). In other variations, the light barrier 350 may be extended only partially into the optical window 340. Still further, in other variations, the light barrier 350 does not contact the optical window 340 of the BVSD 300.

Figure 3B:
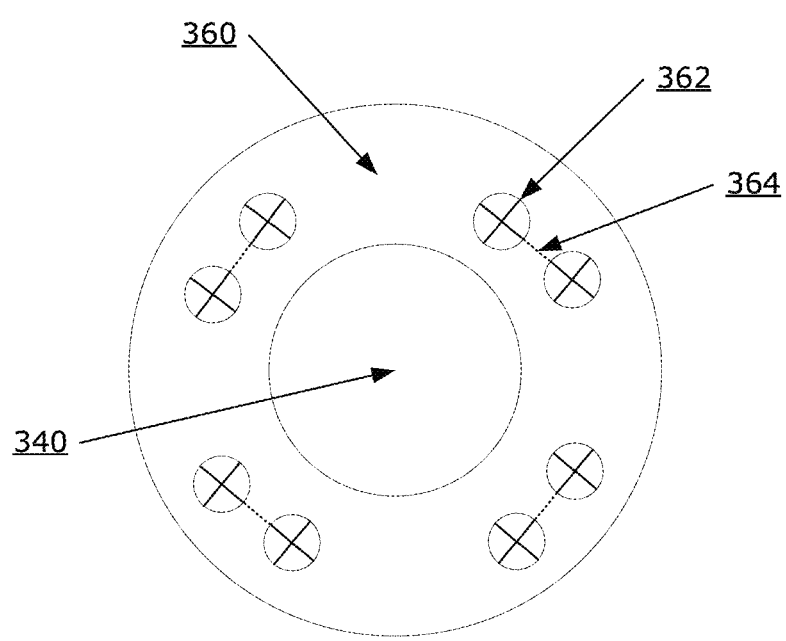
FIG. 3B illustrates an example of a suture skirt for a sensor such as described with FIG. 3A.

FIG. 3B illustrates an embodiment of the suture skirt 360 for BVSD 300. The suture skirt 360 includes suture openings 362 that are configured to provide a maximum number of degrees of freedom for the bladder tissue in the implantation area (e.g., bladder tissue under the BVSD 110/300) so as to not hinder or impede biaxial stretching of the bladder tissue that may occur during normal filling of the bladder. In one variation, the BVSD 300 includes four pairs of suture openings 362 where four suture knots may be respectively tied along a suture path 364 in order to fix the BVSD 300 to an external wall of the bladder (e.g., 102). Such embodiments in which the suture openings 362 are provided as a set number of pairs (e.g., 2, 3, 4, 5, etc.) provide an advantage of minimizing, or at least not impeding or hindering stretching of the bladder when the sutures affix the BVSD 300 to the bladder. As the bladder can continue to stretch, the pairwise arrangement of suture openings 362 allow the bladder to expand naturally (e.g., as if the BVSD 300 was not present), so as to be without unnatural size restrictions or pain to the patient. In other variations, the BVSD 300 may be coated with or otherwise impregnated with a growth factor known in the art to promote encapsulation, such as cellular and/or protein encapsulation as between the BVSD 300 and an external wall of the bladder.

In some variations, the BVSD 300 can become naturally encapsulated, through exposure to the patient's tissue. By way of example, natural encapsulation can result when the BVSD 300 being attached to, or otherwise affixed in position adjacent to or on the patient's bladder, for a sufficient period of time to allow for the natural development of scar tissue and/or protein deposits in surrounding areas of the patient's bladder, in a manner that causes the BVSD 300 to be affixed to the wall of the bladder. The use of such natural processes can provide an additional or alternative attachment mechanism for the BVSD 300 with respect to a patient's bladder wall. Still further, in some eembodiments, the use of a natural process can replace an initial attachment mechanism over time. For example, a suture kit can be used to initially attach the BVSD 300 to the bladder wall, and a natural process can then be allowed or enabled within the patient body to result in the BVSD 300 being substantially affixed and/or in contact with the patient's exterior bladder wall.

FIG. 4A through FIG. 4H illustrate alternative embodiments of a BVSD, in accordance with one or more embodiments. In embodiments as described, BVSD 400 includes a light emitter 410 and a light detector 420, mounted to one another in alternative configurations. In the embodiments of FIG. 4A through FIG. 4D, the light source 410 and the light detector 420 are mounted on a backing 430. In the embodiments of FIG. 4E through FIG. 4H, the light source 410 and the light detector 420 are mounted on an optical window 440.

Figure 4A:
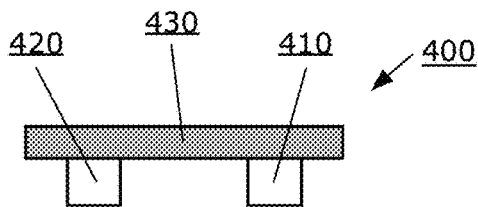
FIG. 4A to FIG. 4H illustrate various examples of a sensor to detect fullness of a bladder of a patient.

In FIG. 4A, the light source 410 and the light detector 420 pair ("410/420 pair") are mounted on the backing 430 in a "no port" configuration, where the 410/420 pair are exposed. In contrast to FIG. 4A, FIG. 4B through FIG. 4D illustrate alternative configurations of the 400 in which the 410/420 pair is hermetically sealed. In FIG. 4B, the device is configured in a "single port" configuration in which the 410/420 pair is hermetically sealed between the backing 430, the optical window 440 and a siding 402. FIG. 4C includes a "dual port" configuration in which a barrier 450 is configured to prevent the direct transmission of light between the 410/420 pair.

The barrier 450 may include alternative configurations, such as characterized by a length of the barrier 450. In the embodiments of FIG. 4C, the barrier 450 is configured to extend from the backing 430 and to/through the optical window 440. In an embodiment of FIG. 4D, the barrier 450 extends from the backing 430 to the optical window 440 but does not extend into the optical window 440. In other variations (not shown here), the barrier 450 may extend partially into the optical window 440. In other embodiments such as depicted by FIG. 3A, the barrier 350 may extend from the optical window, but may not extend fully to the backing 330.

Figure 4E:
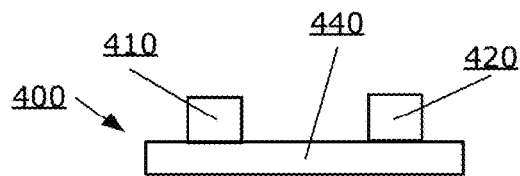
Figure 4B:
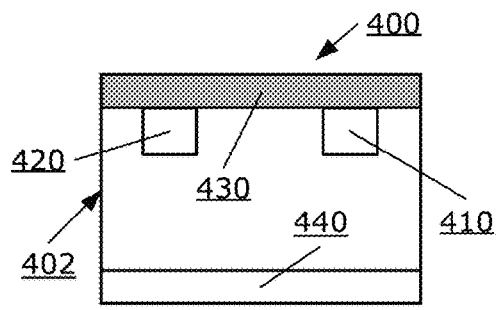
Figure 4F:
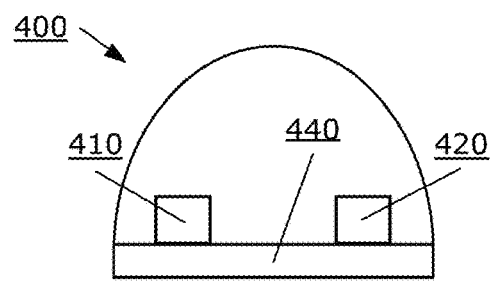
Figure 4C:
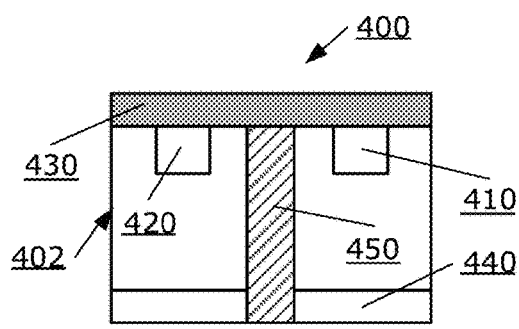
Figure 4G:
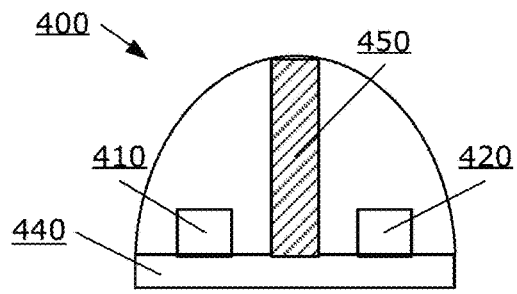
Figure 4D:
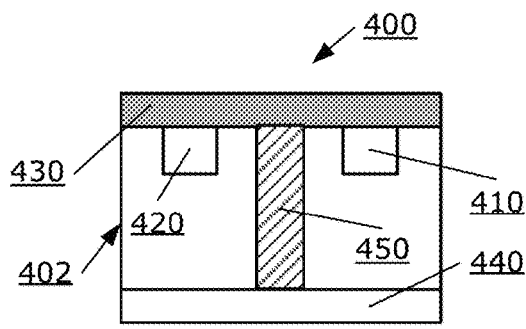
Figure 4H:
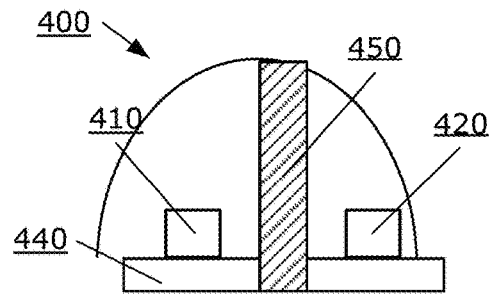

In embodiments of FIG. 4E through FIG. 4H, the 410/420 pair may be mounted on an optical window 440. In the embodiment of FIG. 4E, the 410/420 pair is configured in a "no port-window coupled" configuration, in which the 410/420 pair is exposed to the surrounding environment. In the embodiment of FIG. 4F through FIG. 4H, the 410/420 pair is encapsulated in a protective layer of polymer, epoxy resin or any other biocompatible molded encapsulation. In an embodiment of FIG. 4F, the BVSD 400 is configured in a "no port-window coupled/encapsulated" configuration. In an embodiment of FIG. 4G, the BVSD 400 includes a "dual port" configuration in which the barrier 450 is configured to prevent the direct transmission of light between the 410/420 pair. As discussed above, the barrier 450 may be configured for various lengths to extend to the optical window 440, as depicted in an embodiment of FIG. 4G, or to extend through the optical window, as depicted by an embodiment of FIG. 4H, as well as various other lengths.

In the embodiments of FIG. 4A through 4H, the distance between the light source 410 and the light detector 420 can be fixed. In some variations, as the distance between the light source 410 and the light detector 420 is increased, some improvements in the efficacy of monitoring bladder fullness may occur: (i) the change between the "empty" and "full" measurements of the bladder may increase; and (ii) the signal-to-noise ratio in the signal generated by the BVSD 400 may increase. In some instances, a distance of about 10 mm has been utilized between the light source 410 and the light detector 420, although other distances are contemplated.

EXAMPLES

Various embodiments of the invention are illustrated below for purposes of illustration and without limiting any embodiment or aspect of the invention described to the specific examples.

Example 1 (In Vitro)

This example involved in vitro testing of an embodiment of the BVSD using an explanted porcine bladder.

Figure 5A:
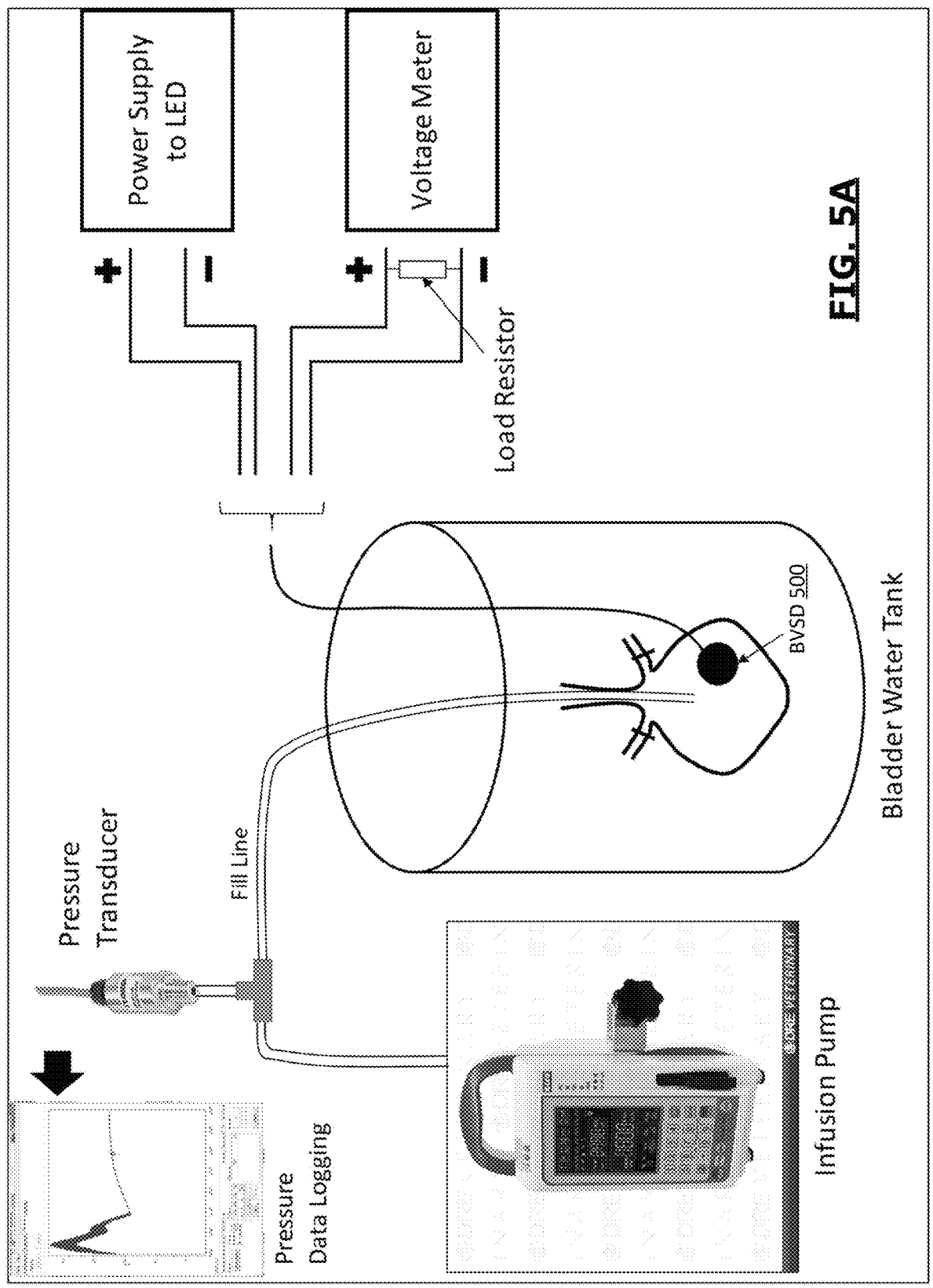
FIG. 5A illustrates an experimental setup to monitor fullness of a bladder, according to one or more examples.

Experimental Setup:

FIG. 5A illustrates a particular experimental in vitro setup to determine the effect of different spacing between the light source (e.g., light source or emitter 310, 410, 510) and the light detector (e.g., detector 320, 420, 520). As illustrated in FIG. 5A, a bladder monitoring system was tested, where the system included a BVSD (e.g., BVSD 300, 400, 500) sutured to an explanted porcine bladder and submerged in water in a bladder water tank. While an infusion pump and pressure transducer combined to provide a bladder fill rate of 360 mL/hr, a power supply was configured to provide power to operate the light source of the BVSD and a voltage meter was configured to measure the corresponding electrical signals generated by the light detector (e.g., a photodiode) of the BVSD.

Figure 5B:
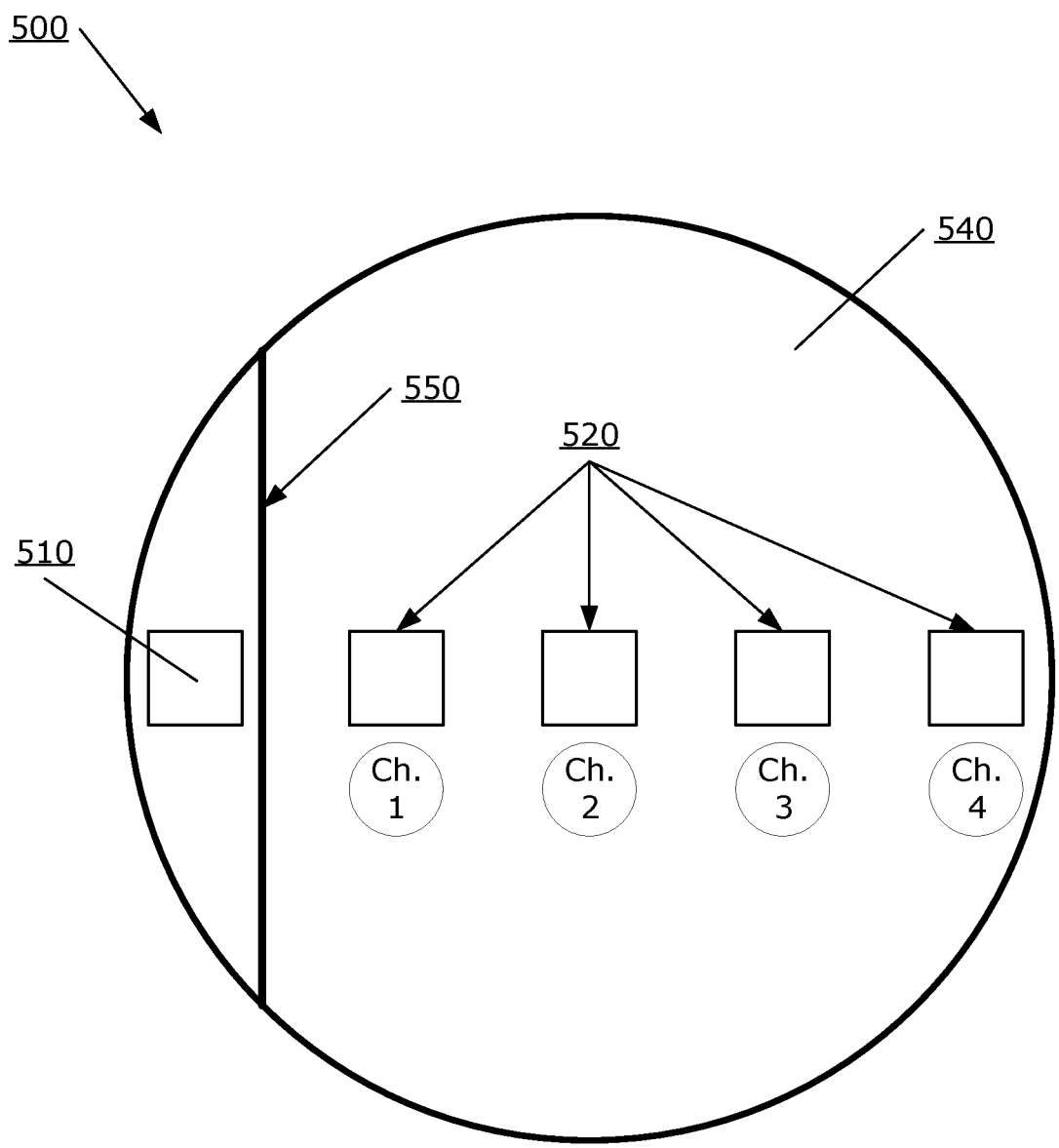
FIG. 5B illustrates an experiment to determine differences in spacing between different channels in the experimental sensor.

FIG. 5B illustrates the experimental configuration of the BVSD 500 for determining whether the spacing of the light source and the light detector pair is related to the resulting change between an empty bladder and a full bladder. The light source 510 and the multiple light detectors 520 were mounted on an optical window 540 and separated by a barrier 550. In an implementation of FIG. 5B, the light source 510 comprises an LED, specifically an APT2012SF4C-PRV LED, and the light detectors 520 each comprise photodiodes ("PD"), specifically, VEMD1060X01 photodiodes, spaced at progressively larger distances from the LED. For example, in one experimental setup, the distance from the center of the LED 510 to the center of the PD 520 positioned in Channel 1 ("Channel 1") measured 2.9 mm; the distance from the center of the LED 510 to the center of the PD 520 positioned in Channel 2 ("Channel 2") measured 5.5 mm; the distance from the center of the LED 510 to the center of the PD 520 positioned in Channel 3 ("Channel 3") measured 8.2 mm; and the distance from the center of the LED 510 to the center of the PD 520 positioned in Channel 4 ("Channel 4") measured 10.4 mm.

The experimental setup depicted in FIG. 5A and FIG. 5B provided an independent evaluation of each LED/PD pair by sequentially energizing each pair spacing and sampling a PD voltage for each while filling the bladder with saline using the infusion pump. Further, each channel was sequentially turned on for a period of 1 second and the corresponding PD voltage was sampled for each individual channel of LED emission. Utilizing a fill rate of 360 mL/hr, the mean bladder volume change was calculated using the first and last 100 samples of each channel's recorded electrical signals.

Figure 6:
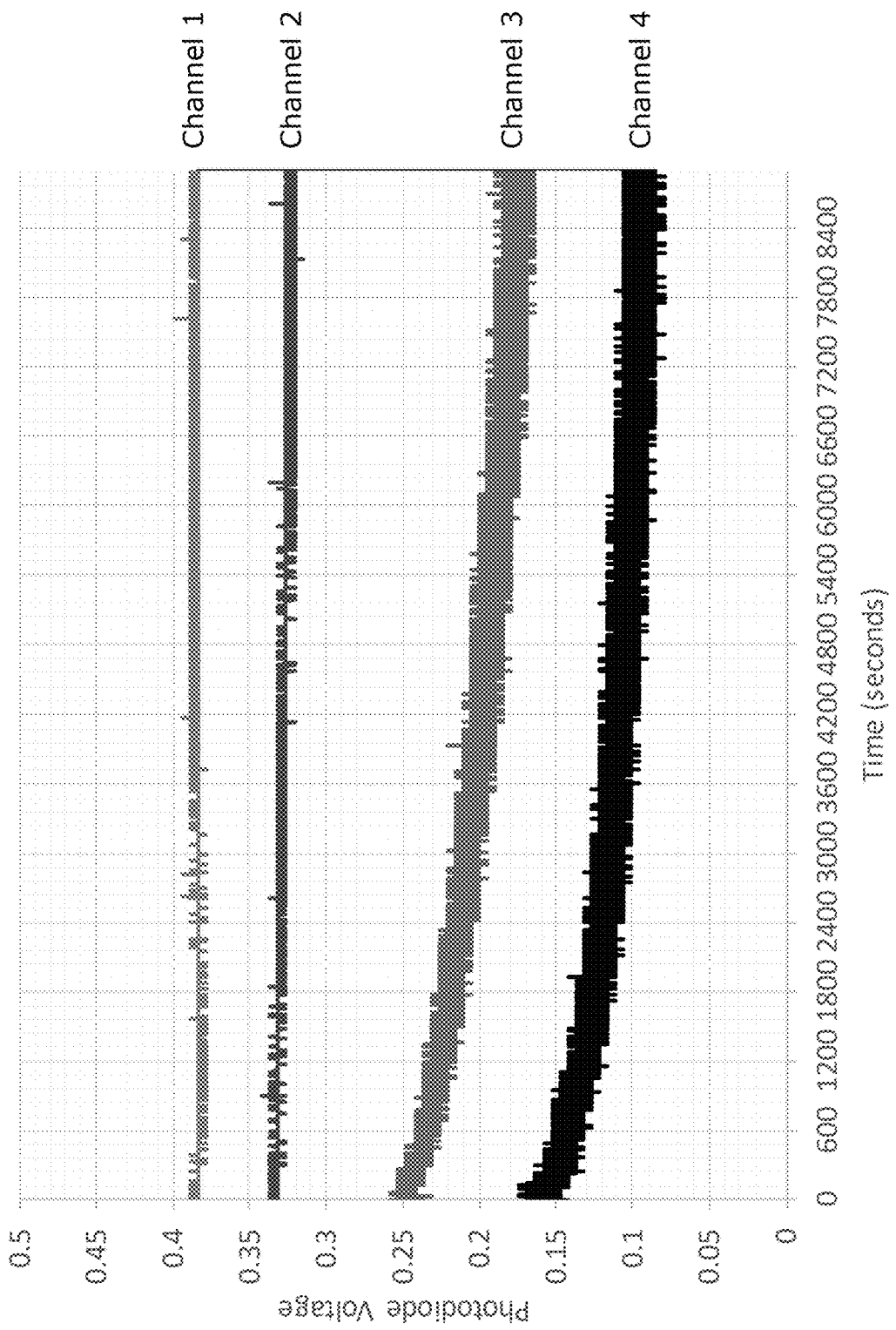
FIG. 6 is a graph of a measured photodiode voltage versus bladder fill time, illustrating a response of a bladder monitoring system using a sensor of FIG. 5B.
Figure 7:
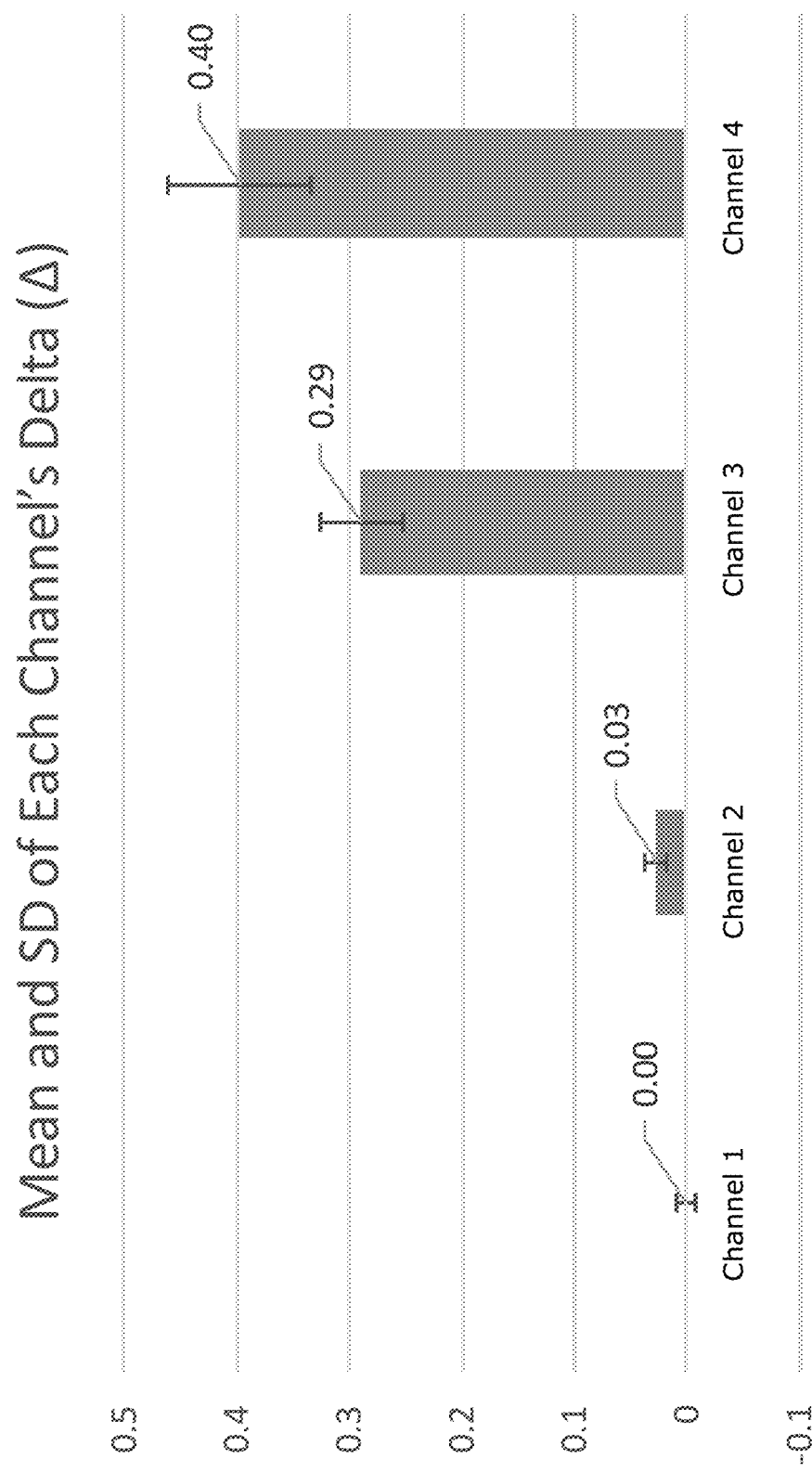
FIG. 7 is a graph of the mean and standard deviation of each channel's delta ($\Delta$) for a sensor of FIG. 5B.

Results:

FIG. 6 is a graphical representation of the PD voltage measured over the course of filling the bladder. The graph illustrates the response of different spacing configurations of the LED and PD of a system utilizing an example BVSD (corresponding to channels 1-4 shown in FIG. 5B) to bladder filling/stretching. As depicted in FIG. 6, the bladder volume change, which is the difference in PD voltage measured over time as the bladder is filled, becomes greater from Channel 1 to Channel 4. In other words, the bladder volume change became greater as the distance between the LED 510 and the PD 520 became greater. In addition, FIG. 7 illustrates this phenomenon in terms of the mean and standard deviation of each channel's change. The greatest mean and standard deviation was observed in Channel 4 in which the PD 520 was configured to be positioned furthest from the LED 510 relative to the other channels. This result was unexpected in at least two respects discussed below.

First, one of skill in the art would have expected that the LED/PD pair positioned closest together (e.g., Channel 1) relative to the other channels would yield the greatest mean and standard deviation over time as the bladder was filled. This expected result is based on the decreased loss of light from scattering when the LED and PD are closer together, as well as the LED and PD being more closely aligned with the angle of reflectance of light from the skin surface when closer together.

Second, prior research has indicated that the measured intensity of reflected light from a stretched skin surface increased in a linear fashion with increased stretching of the skin surface. See Federici, J. et al., Noninvasive-Light Reflection Technique for Measuring Soft Tissue Stretch. Applied Optics. 1999 Nov. 1; 38(31):6653-60. In contrast, in the example discussed above case, the intensity of the measured light decreased with increased stretching of the bladder wall (e.g. via filling of the bladder) and did so in what appeared to be a non-linear fashion. So here again, the experimental results were contrary to what one skilled in the art would have expected for experiments conducted using embodiments of the BVSD as they ran contrary to the state of the art.

Example 2 (In Vivo Studies)

This example involved in vivo testing of an embodiment of the BVSD in a porcine model.

Figure 8A:
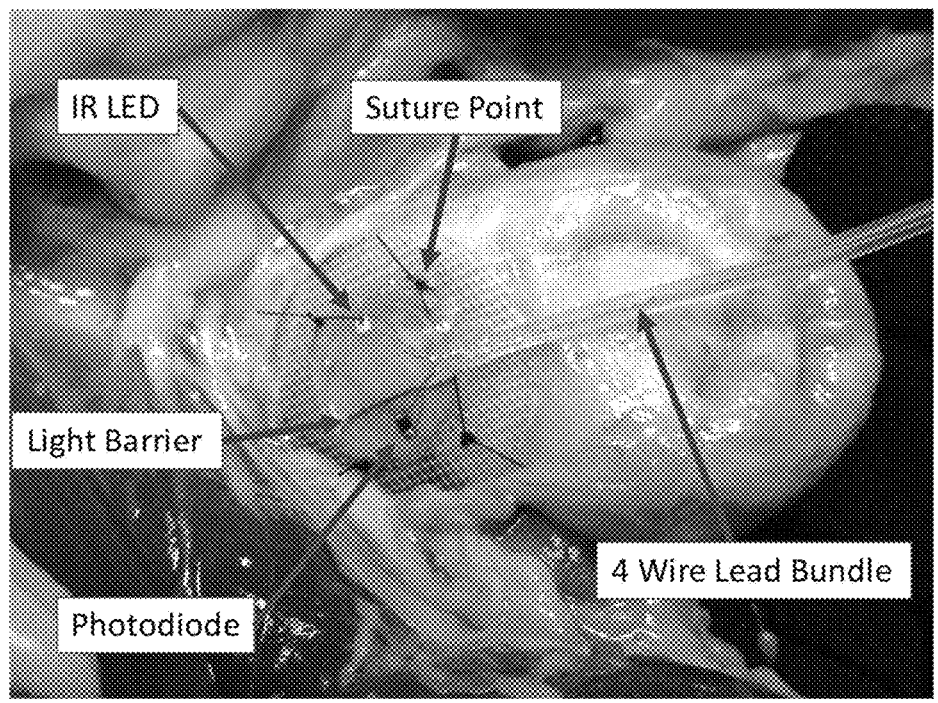
FIG. 8A and FIG. 8B are photographs illustrating a set up for a porcine in vivo test of an example sensor for use with the porcine bladder, as described by various examples.
Figure 8B:
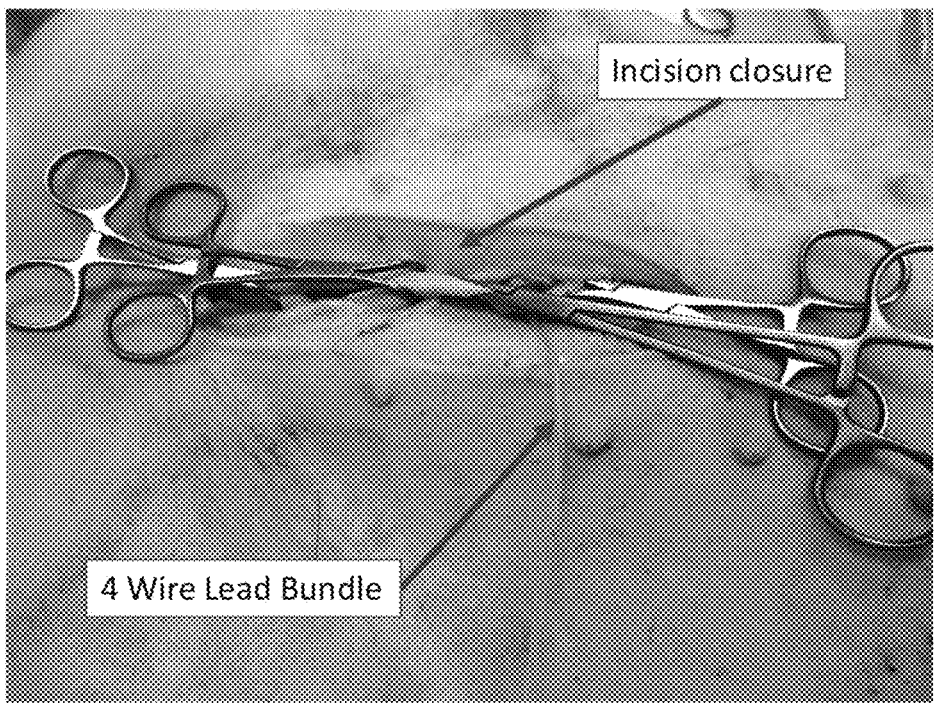

Experimental Setup:

A 35 kg pig was obtained in excellent condition after the humane endpoint of another study (separate from the BVSD study), and in accordance with good animal re-use policy. The pig bladder was catheterized and connected to DRE Infusion Pump set for 420 mL/hr. An incision was made and an BVSD sensor was sutured to the surface of the bladder, as shown in FIG. 8A and FIG. 8B. The incision was closed and a constant rate infusion of saline began. The voltage output of the BVSD photodiode across a 10 k load resistor was recorded for the duration of the fill of the bladder which was about 1 hour. The sample rate was 1 sample per second, so for the one-hour duration of the experiment there were 3600 samples for a 420 mL fill of the bladder volume. Data were recorded using a Keithley DMM as used in bench top testing.

Figure 9:
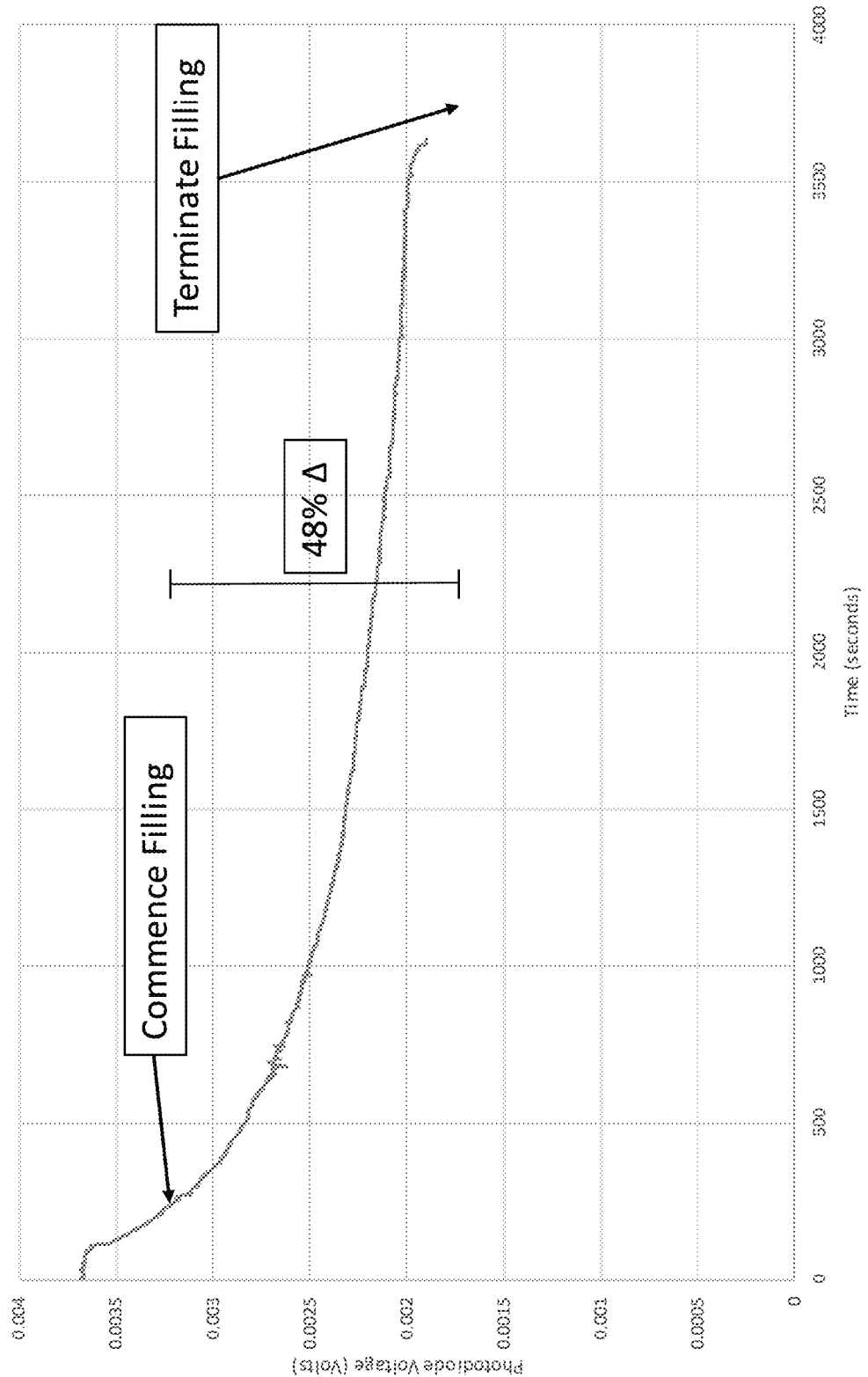
FIG. 9 is a graph of measured photodiode voltage versus bladder fill time, as demonstrated with examples of FIG. 8A and FIG. 8B.

Results:

The results, shown in FIG. 9, show that the mean change was 48% with a standard deviation of 0.2%.

Figure 10:
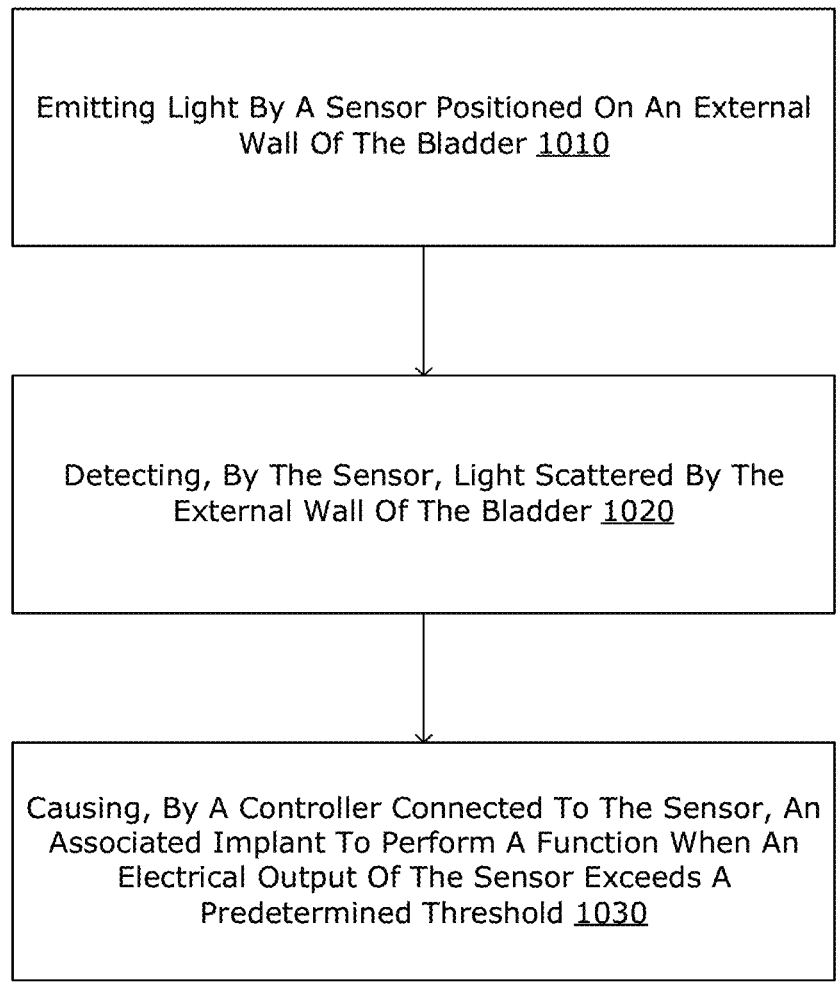
FIG. 10 illustrates an example method to monitor fullness of a patient's bladder.

FIG. 10 illustrates an example method to monitor fullness of a patient's bladder. An example such as described by an example of FIG. 10 can be implemented using devices and sensors such as described with other examples, including those with FIG. 1A through FIG. 9. Accordingly, reference may be made to elements described with FIG. 1A through FIG. 9 to illustrate suitable components for implementing a step or sub-step being described.

According to some examples, the fullness of a patient's bladder can be monitored using an active optical sensor that is positioned on an external wall of the patient's bladder, where the sensor functions to emit light on and/or into the wall of the bladder (1010). The sensor may include at least one pair of suture openings on a tissue contacting surface of the sensor that allows the sensor to be fixed to an external wall of the bladder (e.g., 102) without piercing an internal wall of the bladder (e.g., 104). This approach reduces a risk of infection that persists in some conventional approaches which leave an indwelling catheter or other device within the bladder. The sensor may also include an optical window. As the efficacy of the optical window may be reduced when the optical window is not directly coupled to a surface of the bladder wall, in some variations, the optical sensor may include as many as four pairs of suture openings (e.g., in four corners of a suture skirt) to provide direct coupling between a tissue contacting surface of the device and an external wall of the bladder, but also to enable the bladder tissue of the implantation site to stretch. Other configurations and other numbers of suture openings are also contemplated.

Further, the sensor detects light scattered by the external wall of the bladder (1020). In variations, the sensor may operate with a range of wavelengths that enable a range of tissue penetration depths. For example, referring to FIG. 1B, one wavelength range may only cause light scattering in the bladder tissue of a proximal portion of external bladder wall of the bladder (e.g., between 102 and 104), as depicted in the first mode. Whereas another wavelength may cause light scattering in the bladder tissue of a distal wall of the bladder (e.g., 106), as depicted in the second mode.

In the method of FIG. 10, the controller causes an associated implant to perform a function when an electrical output of the sensor exceeds a predetermined threshold (1030). The electrical output generated by the sensor may be proportional to the amount of light scattered by the bladder and can be compared to a predetermined range of outputs representing an "empty" bladder and a "full" bladder (e.g., Δ). To minimize or eliminate the direct transmission of light between the light source and the light detector, which may adversely affect the accuracy of the light scattering measurements, a light barrier may be positioned between the light source and the light detector. In examples such as illustrated by FIG. 3A, the light barrier 350 may extend into the optical window 340 to form part of the tissue contacting surface of the BVSD 300. In a variation illustrated in FIG. 4D and FIG. 4G, the light barrier 450 may extend to contact the optical window 440 but may not extend within the optical window 440 to form part of the tissue contacting surface.

In various embodiments, the controller may also be configured to determine (e.g., by software or hardware) whether a percentage change in the output received by the sensor exceeds a predetermined threshold. In one variation, when the controller determines that the percentage change in the electrical output exceeds the predetermined threshold, the controller may cause an associated implant to notify the patient of a level of fullness of the bladder, or may cause an associated implant to induce micturition.

Figure 11:
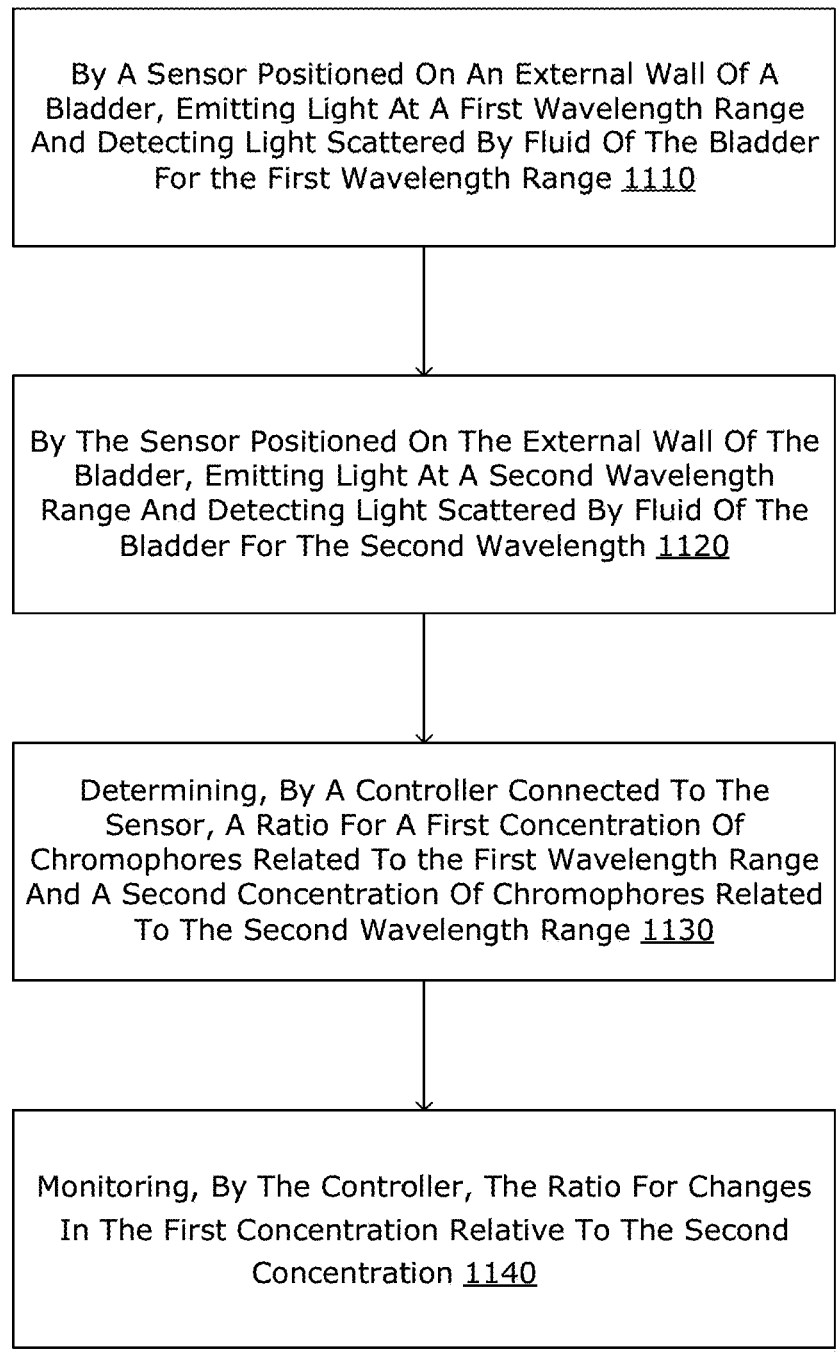
FIG. 11 illustrates an example method to determine relative concentrations of chromophores such as bacteria or blood present in a bladder fluid of a patient.

FIG. 11 illustrates an example method to determine relative concentrations of chromophores present in a bladder fluid of a patient. Such chromophores include one or more of bacteria (or other single cell organism), protein and blood. Examples such as described by FIG. 11 can be implemented using embodiments of devices and sensors, such as described with examples of FIG. 1A through FIG. 9. Accordingly, reference may be made to elements described with FIG. 1A through FIG. 9 to illustrate suitable components for implementing a step or sub-step being described.

With reference to an example of FIG. 11, a sensor positioned on an external wall of the bladder may emit light at a first wavelength range, and further detect light scattered by fluid of the bladder for the first wavelength range (1140). For example, the sensor may emit ultraviolet light, where bacteria and protein have the highest optical absorption.

Further, the sensor may emit light at a second wavelength range and detect light scattered by fluid of the bladder (1120). For example, the sensor may emit light in the 532-585 nm range, where oxyhemoglobin and deoxyhemoglobin have well-established absorption peaks.

The controller, which connects to the sensor, may determine a ratio for a first concentration of chromophores related to the first wavelength range and a second concentration of chromophores related to the second wavelength range (1130). For example, the controller may utilize an algorithm or equation (e.g., Beer-Lambert Law) to solve for the concentration of protein and bacteria present in the bladder. For example, the controller may utilize the following equation:

$$I_{\lambda uv} = (\varepsilon_{protein+bacteria})(\lambda_{UV})(C_{bacteria+protein})$$

Where $I_{\lambda uv}$ represents the current measured from the sensor, $\varepsilon_{protein+bacteria}$ represents the molar extinction coefficient of protein plus bacteria (known quantity), $\lambda_{uv}$ represents the wavelength of emitted light (known quantity), and $C_{bacteria+protein}$ represents the relative concentration ratio of protein plus bacteria.

The controller may determine the second concentration of chromophores present in the bladder by similar means. For example, the controller may utilize an algorithm or equation (e.g., Beer-Lambert Law) to solve for the concentration of hemoglobin present in the bladder. For example, the controller may utilize the following equation:

$$I_{\lambda 532-585} = (\varepsilon_{hemoglobin})(\lambda_{532-585})(C_{hemoglobin})$$

Where $I_{\lambda 532-585}$ represents the current measured from the light sensor, $\varepsilon_{hemoglobin}$ represents the molar extinction coefficient of hemoglobin (known quantity), at a particular wavelength $\lambda$, $\lambda_{532-585}$ represents the wavelength of emitted light (known quantity) in the specified range of 532 to 585 nm, and $C_{hemoglobin}$ represents the relative concentration ratio of hemoglobin.

The controller may monitor the ratio for changes in the first concentration relative to the second concentration (1140). Additionally, a third wavelength may be emitted and sensed as a control or baseline concentration. This may be in the near infrared region far removed from the absorption peaks used in the previous algorithm. Thus, a system of 3 equations can be obtained, and the relative concentrations of protein/bacteria and hemoglobin can be measured against a third control relative concentration.

CONCLUSION

It is contemplated for embodiments described herein to extend to individual elements and concepts described herein, independently of other concepts, ideas or systems, as well as for examples to include combinations of elements recited anywhere in this application. Although embodiments are described in detail herein with reference to the accompanying drawings, it is to be understood that the concepts are not limited to those precise examples. Accordingly, it is intended that the scope of the concepts be defined by the following claims and their equivalents. Furthermore, it is contemplated that a particular feature described either individually or as part of an embodiment can be combined with other individually described features, or parts of other embodiments, even if the other features and examples make no mention of the particular feature. Thus, the absence of describing combinations should not preclude having rights to such combinations.

The foregoing description of various embodiments of the invention has been presented for purposes of illustration and description. It is not intended to limit the invention to the precise forms disclosed. Many modifications, variations and refinements will be apparent to practitioners skilled in the art. For example, examples of the device can be sized and otherwise adapted for various pediatric and neonatal applications as well as various veterinary applications. They may also be adapted for the urinary tracts of both male and females. Further, those skilled in the art will recognize, or be able to ascertain using no more than routine experimentation, numerous equivalents to the specific devices and methods described herein. Such equivalents are considered to be within the scope of the present invention and are covered by the appended claims below.

Elements, characteristics, or acts from one embodiments can be readily recombined or substituted with one or more embodiments, characteristics or acts from other examples to form numerous additional embodiments within the scope of the invention. Moreover, elements that are shown or described as being combined with other elements, can, in various embodiments, exist as standalone elements. Also for any positive recitation of an element, characteristic, constituent, feature or step embodiments of the invention specifically contemplate the exclusion of that element, value, characteristic, constituent, feature or step. Hence, the scope of the present invention is not limited to the specifics of the described examples, but is instead limited solely by the appended claims.

What is claimed is:

1. A bladder monitoring system comprising:
   a sensor device fixedly positionable on an external wall of the bladder without piercing an internal wall of the bladder, the sensor device including (i) a light emitter positioned at the external wall of the bladder to emit light to targeted regions within the bladder in a plurality of wavelength ranges, and (ii) a detector positioned to detect reflected emitted light based on the emitted light,
   wherein, in a first mode, the light emitter targets the emitted light, in a first of the plurality of wavelength ranges, to a first region of the targeted regions between the external wall and the internal wall of the bladder to determine bladder fullness based on a correlation between light reflected back to the detector and fullness of the bladder,
   wherein, in a second mode, the light emitter targets the emitted light, in a second of the plurality of wavelength ranges, from a proximal wall of the bladder relative to the sensor device to a second region of the targeted regions that coincides with a distal interior wall of the bladder to determine a time of flight measurement based on the light reflected back from the distal interior wall to calculate distance between the proximal wall and the distal wall;
   wherein, in a third mode, the light emitter targets the emitted light to a third region of the targeted regions. the third region being submerged below a fluid level in the bladder, to determine differences in refractive index between wall tissue of the bladder and liquid contents of the bladder;
   wherein the sensor device generates an output signal that is indicative of the reflected emitted light detected by the detector; and a controller operatively coupled to the sensor device, the controller including logic executed by one or more processors of the controller, causing the one or more processors to:
- select the targeted region for directing the emitted light such that different types of information can be determined about the bladder, the targeted region being selected from possibilities including the first region, the second region, or the third region;
- operate the sensor device in the first mode to receive the output signal from the sensor device in the first mode indicative of the fullness of the bladder;
- operate the sensor device in the second mode to receive the output signal from the sensor device in the second mode indicative of the distance between the proximal wall and the distal wall; and
- operate the sensor device in the third mode to receive the output signal from the sensor device in the third mode indicative of the differences in the refractive index between the wall tissue of the bladder and the liquid contents of the bladder.

2. The system of claim 1, wherein the output signal of the sensor device is indicative of an amount of emitted light that is scattered by the external wall of the bladder.

3. The system of claim 1, wherein the output signal of the sensor device is indicative of an intensity of reflected emitted light.

4. The system of claim 1, wherein the executed logic causes the one or more processors to further determine the degree of bladder fullness based on an inverse relationship between the degree of bladder fullness and a magnitude of the output signal of the sensor device.

5. The system of claim 1, wherein the controller is configured to generate an output that is detectable by a patient when the determined degree of bladder fullness exceeds a threshold.

6. The system of claim 1, wherein the controller is configured to send a notification to a mobile device of a patient when the determined degree of bladder fullness exceeds a threshold.

7. The system of claim 1, wherein the sensor device includes at least one pair of suture openings, the at least one pair of suture openings configured to enable sutures to affix the sensor device to the external wall of the bladder without piercing the internal wall of the bladder.

8. The system of claim 1, wherein light emitter of the sensor device is further configured to emit light to reflect from an interior wall of the bladder that is distal to a location of the sensor device.

9. The system of claim 1, wherein the controller is configured to cause an associated urinary control apparatus to perform a function when the output signal of the sensor device exceeds a predetermined threshold.

10. The system of claim 9, wherein the function performed by the urinary control apparatus includes inducing micturition.

11. The system of claim 10, wherein the controller is integrated with the urinary control apparatus.

12. The system of claim 10, wherein the controller is separate from the urinary control apparatus.

13. The system of claim 1, wherein a spacing between the light emitter and the detector is in a range from about 8.2 to 10.4 mm.

14. The system of claim 1, wherein the sensor device is coated with or otherwise impregnated with a growth factor to promote cellular and/or protein encapsulation between the sensor device and the external wall of the bladder.

15. The system of claim 1, wherein, in a fourth mode, the light emitter targets the emitted light to a fourth region of the targeted regions, the fourth region being further submerged below the fluid level in the bladder as compared to the third region, wherein the possibilities for the targeted region further includes the fourth region, and wherein the controller is further configured to operate the sensor device in the fourth mode to receive the output signal from the sensor device indicative of concentration of solids that is present in the liquid contents of the bladder.

16. A modal sensor device for detecting fullness of a bladder of a patient, the sensor device comprising:
- a base surface to fixedly attach onto an external wall of the bladder without piercing an internal wall of the bladder;
- a light source coupled to the base surface, the light source configured to emit light in a plurality of wavelength ranges at the external wall to targeted regions within the bladder; and
- a light detector positioned to detect light scattered from the external wall of the patient's bladder based on the emitted light;
- wherein, in a first mode, the light source targets the emitted light, in a first of the plurality of wavelength ranges, to a first region of the targeted regions between the external wall and the internal wall of the bladder to determine bladder fullness based on a correlation between light reflected back to the detector and fullness of the bladder,
- wherein, in a second mode, the light source targets the emitted light, in a second of the plurality of wavelength ranges, from a proximal wall of the bladder relative to the sensor device to a second region of the targeted regions that coincides with a distal interior wall of the bladder to determine a time of flight measurement based on the light reflected back from the distal interior wall to calculate distance between the proximal wall and the distal wall,
- wherein, in a third mode, the light source targets the emitted light to a third region of the targeted regions, the third region being submerged below a fluid level in the bladder, to determine differences in refractive index between wall tissue of the bladder and liquid contents of the bladder,
- wherein the detector is configured to
  - select the targeted region for directing the emitted light such that different types of information can be determined about the bladder in an output signal, the targeted region being selected from possibilities including the first region, the second region, or the third region,
  - operate the sensor device in the first mode to receive the output signal from the sensor device in the first mode indicative of the fullness of the bladder;
  - operate the sensor device in the second mode to receive the output signal from the sensor device in the second mode indicative of the distance between the proximal wall and the distal wall; and
  - operate the sensor device in the third mode to receive the output signal from the sensor device in the third mode indicative of the differences in the refractive index between the wall tissue of the bladder and the liquid contents of the bladder.

17. The sensor device of claim 16, wherein the output signal is configured to be utilized by a controller operatively coupled to the sensor device to determine the tissue thickness of the bladder and when the degree of fullness of the bladder exceeds a predetermined threshold.

18. The sensor device of claim 16, wherein the light source is a light-emitting diode.

19. The sensor device of claim 16, wherein the light detector is a photodiode.

20. The sensor device of claim 16, further comprising an optical window formed from sapphire.

21. The sensor device of claim 16, further comprising an optical barrier positioned and configured to prevent direct transmission of light between the light source and the light detector.

22. A method to monitor fullness of a bladder of a patient, the method comprising:

emitting light to targeted regions within the bladder, by a light emitter of a modal sensor device, in a plurality of wavelength ranges onto an external wall of the bladder, wherein the sensor device is affixed to the external wall of the bladder without piercing an internal wall of the bladder;

detecting, by a detector of the sensor device, light reflected by the external wall of the bladder based on the emitted light;

generating, by the sensor device, an output signal corresponding to the light reflected by the external wall based on the emitted light;

operating, by a controller, the sensor device in a first mode to receive the output signal from the sensor device in the first mode, wherein, in the first mode, the light emitter targets the emitted light, in a first of the plurality of wavelength ranges, to a first region of the targeted regions between the external wall and the internal wall of the bladder to determine bladder fullness based on a correlation between light reflected back to the detector and fullness of the bladder;

operating, by the controller, the sensor device in a second mode to receive the output signal from the sensor device in the second mode, wherein, in the second mode, the light emitter targets the emitted light, in a second of the plurality of wavelength ranges, from a proximal wall of the bladder relative to the sensor device to a second region of the targeted regions that coincides with a distal interior wall of the bladder to determine a time of flight measurement based on the light reflected back from the distal interior wall to calculate distance between the proximal wall and the distal wall;

operating, by the controller, the sensor device in a third mode to receive the output signal from the sensor device in the third mode, wherein, in the third mode, the light emitter targets the emitted light to a third region of the targeted regions, the third region being submerged below a fluid level in the bladder, to determine differences in refractive index between wall tissue of the bladder and liquid contents of the bladder;

selecting the targeted region for directing the emitted light such that different types of information can be determined about the bladder, the targeted region being selected from possibilities including the first region, the second region, or the third region;

operating the sensor device in the first mode to receive the output signal from the sensor device in the first mode indicative of the fullness of the bladder;

operating the sensor device in the second mode to receive the output signal from the sensor device in the second mode indicative of the distance between the proximal wall and the distal wall; and operating the sensor device in the third mode to receive the output signal from the sensor device in the third mode indicative of the differences in the refractive index between the wall tissue of the bladder and the liquid contents of the bladder.

23. The method of claim 22, further comprising:

performing a function, by a urinary control apparatus associated with the sensor device, when the degree of fullness exceeds a predetermined threshold.

24. The method of claim 23, wherein the urinary control apparatus comprises a pudendal neural stimulation device.

25. The method of claim 23, wherein the function comprises sending a notification to the patient.

26. The method of claim 25, wherein the notification includes information corresponding to the degree of fullness of the patient's bladder or a need to urinate.

27. The method of claim 23, wherein the function comprises electronic initiation of urination.

28. The method of claim 23, further comprising affixing the sensor device in position adjacent to or on the bladder to allow for natural development of scar tissue and/or protein deposits in surrounding areas of the bladder to affix the sensor device to the external wall of the bladder without piercing the internal wall of the bladder.

* * * * *